(12) United States Patent
Farrell (10) Patent No.: US 8,324,197 B2
(45) Date of Patent: Dec. 4, 2012

(54) TRANSPLATINUM COMPLEXES WITH $N_2O_2$ DONOR SETS AS CYTOTOXIC AND ANTITUMOR AGENTS

(75) Inventor: Nicholas P. Farrell, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 1722 days.

(21) Appl. No.: 11/502,621

(22) Filed: Aug. 11, 2006

(65) Prior Publication Data

US 2007/0082882 A1    Apr. 12, 2007

Related U.S. Application Data

(60) Provisional application No. 60/707,176, filed on Aug. 11, 2005.

(51) Int. Cl.
  *A61K 31/555*    (2006.01)
  *C07F 15/00*     (2006.01)
(52) U.S. Cl. ............. 514/184; 544/225; 546/2; 548/101

(58) Field of Classification Search .................. 514/184; 544/225; 546/2; 548/101
See application file for complete search history.

(56) References Cited

U.S. PATENT DOCUMENTS 6,894,049 B1 *    5/2005  Wong et al. ................ 514/252.1

FOREIGN PATENT DOCUMENTS

EP    0727430 A1 *   8/1996

OTHER PUBLICATIONS

Rashan et al., "In vitro antitumor activity of platinum (II) complexes with various nitrogen containing ligands", Biologia, 1998, 53(3), abstract.*

* cited by examiner

*Primary Examiner* — Jason M Sims
*Assistant Examiner* — Zohreh Vakili
(74) *Attorney, Agent, or Firm* — Whitham, Curtis, Christofferson & Cook, P.C.

(57) ABSTRACT

Trans-platinum compounds comprising carboxylato groups are disclosed, with anti-cancer usefulness. The carboxylato groups participate in solubilizing trans-platinum compounds to which they are attached.

8 Claims, 2 Drawing Sheets

TRANSPLATINUM COMPLEXES WITH $N_2O_2$ DONOR SETS AS CYTOTOXIC AND ANTITUMOR AGENTS

RELATED APPLICATION

This application claim priority from U.S. provisional application Ser. No. 60/707,176 filed Aug. 11, 2005 for "Trans-platinum complexes with $N_2O_2$ donor sets as cytotoxic and antitumor agents" by Nicholas Farrell.

STATEMENT REGARDING FUNDING

This invention was made using funds from grants from the National Science Foundation having grant number CHE034205. The United States government may have certain rights in this invention.

FIELD OF THE INVENTION

The invention generally relates to novel cytotoxic and antitumor platinum II compounds. In particular, the invention provides trans-platinum complexes with $N_2O_2$ donor sets which are stable, water soluble, and display a low level of cross resistance with traditional cis-Pt anticancer drugs.

BACKGROUND OF THE INVENTION

Current anti-cancer drugs based on platinum (cisplatin (i.e., cis-[$PtCl_2(NH_3)_2$], cis-DDP); carboplatin (i.e., cis-[Pt(CBDCA)($NH_3$)$_2$], (CBDCA=cyclobutane-1,1-dicarboxylate)); and oxaliplatin (i.e., [Pt(ox)(dach)] (dach=1,2-diaminocyclohexane, ox=oxalato)) share similar clinical properties due to their structural similarities (namely, their cis geometry around the platinum atom). Their mechanisms of action, especially with respect to the purported target DNA, are also consequently very similar. While these are the drugs of choice for the treatment of many types of tumors, with time, tumor cells develop resistance to their cytotoxic effects. The hope in the search for new platinum-based drugs with novel pharmacological properties lies in finding structurally new compounds with fundamentally different mechanisms of action. Such drugs would be useful both on a stand-alone basis for cancer therapy, and would be of particular interest for treating tumors that have become resistant to traditional Pt-based drugs.

For a long time, it was widely believed that, to be cytotoxic and antitumor active, a platinum drug must have a cis geometry with general formula cis-[$PtX_2(am(m)ine)_2$] where X is considered the leaving group, usually chloride or $X_2$ is a bidentate carboxylate such as 1,1-cyclobutanedicarboxylate (CBDCA) or oxalate. The am(m)ine is the donor ligand and is often $NH_3$ or (amine)$_2$ can be a bidentate amine such as 1,2-diaminocyclohexane. The three clinically approved drugs in the United States—cisplatin, carboplatin and oxaliplatin— are all covered by this general formula.

One approach to expand the anticancer spectrum of platinum agents has been to examine structurally unique platinum agents. Through this approach, polynuclear platinum compounds (e.g., trinuclear BBR3464) have emerged as a class. (Farrell, N: Polynuclear Drugs. Metal Ions in Biol. Sys. 41:252-296 (2004); Farrell, N.: Platinum Anti-cancer drugs. From Laboratory to Clinic. ACS Symposium Series 903 "Medicinal Inorganic Chemistry," Sessler, J. A., Doctorow, S. E., McMurry, T. J. and Lippard, S. J. Eds., 62-79 (2005).

Another approach has been to explore the trans geometry. Farrell, N., Current status of structure-activity relationships of platinum anti-cancer drugs: activation of the trans geometry, Met. Ions Biol. Syst., 1996, 32, 251-296; Intini, F. P.; Boccarelli, A.; Francia, V. C.; Pacifico, C. Sivo, M. F.; Natile, G.; Giordano, D.; Rinaldis, P.; Coluccia, M., Platinum complexes with imino ethers or cyclic ligands mimicking imino ethers: synthesis, in vitro antitumour activity, and DNA interaction properties, J. Biol. Inorg. Chem., 2004, 9, 768-780. The paradigm for the early structure activity relationships (SARs) was that the trans geometry, trans-[$PtCl_2(NH_3)_2$] (trans-DDP) was therapeutically inactive.

Substitution of the $NH_3$ group by a sterically hindered planar amine trans-[$PtCl_2(L)(L')$] (L=$NH_3$, L'=pyridine, quinoline, thiazole, etc. and/or L=L'=pyridine or thiazole) gives transplanaramine (TPA) compounds with cytotoxicity to cisplatin in human tumor cell-lines. (van Beusichem, M.; Farrell, N., Activation of the trans geometry in platinum antitumor complexes. Synthesis, characterization, and biological activity of complexes with the planar ligands pyridine, N-methylimidazole, thiazole, and quinoline. Crystal and molecular structure of trans-dicholorobis(thiazole)platinum(II), Inorg. Chem. 1992, 31, 634-639; Farrell, N.; Kelland, L. R.; Roberts, J. D.; van Beusichem, M., Activation of the trans geometry in platinum antitumor complexes: a survey of the cytotoxicity of trans complexes containing planar ligands in murine L1210 and human tumor panels and studies on their mechanism of action, Cancer Res., 1992, 52, 5056-5072.) Use of the planar amine enhances cytotoxicity up to 100-fold over trans-[$PtCl_2(NH_3)_2$]. Further, the compounds generally maintain cytotoxicity in cisplatin-resistant lines.

Since those initial reports by Farrell et al., other groups confirmed the effects of a sterically demanding group in modulation of the cytotoxicity of the transplatinum structure—amines used include cyclohexylamine (Mellish, K. J.; Barnard, C. F. J.; Murrer, B. A.; Kelland, L. R., DNA-binding properties of novel cis- and trans-platinum-based anticancer agents in 2 human ovarian carcinoma cell lines, Int. J. Cancer, 1995, 62, 717-723), branched aliphatic amines (Monterro, E. I.; Diaz, S.; Gonzalez-Vadillo, A. M.; Perez, J. M.; Alonso, C., Navarro-Ranninger, C., Preparation and Characterization of Novel trans-[$PtCl_2$(amine)(isopropylamine)] Compounds: Cytotoxic Activity and Apoptosis Induction in ras-Transformed Cells, J. Med. Chem., 1999, 42, 4264-4268), piperzine, piperidine (Khazanov E.; Barenholz Y.; Gibson D.; Najajreh Y., Novel apoptosis-inducing trans-platinum piperidine derivatives: synthesis and biological characterization, J. Med. Chem. 2002, 45, 5196-204; Najajreh Y.; Perez J. M.; Navarro-Ranninger, C.; Gibson, D. Novel soluble cationic trans-diaminedichloroplatinum(II) complexes that are active against cisplatin resistant ovarian cancer cell lines, J. Med. Chem. 2002, 45, 5189-95) and iminoethers (Intini et al., supra). In general the cytotoxicity of these various compounds is in the 1-20 μM range and is characterized by lack of cross-resistance to cisplatin. The DNA binding profiles of these various compounds show a wide diversity in comparison to those of the cisplatin family. The discovery that trans compounds of formula trans-[$PtX_2$(amine)$_2$] or trans-[$PtX_2$(iminoether)$_2$] can also be cytotoxic has opened a new opportunity in the search of new drugs with cytotoxicity profiles complementary to that of the known clinical agents. Substitution of the $NH_3$ group by a sterically hindered planar amine trans-[$PtCl_2(L)(L')$] (L=$NH_3$, L'=pyridine, quinoline, thiazole, etc. and/or L=L'=pyridine or thiazole) gives "transplanaramine" (TPA) compounds with cytotoxicity comparable to cisplatin in human tumor cell lines. A study of the cytotoxicity of the trans-[$PtCl_2(L)(L')$] series across the NCI human tumor cell line panel showed a unique profile and activity in both cisplatin and oxaliplatin-resistant cells (Fojo T, Farrell, N, Ortuzar, W., Tanimura, H., Weinstein, J., and Myers, T. G.: Identification of non-cross-resistant platinum compounds with novel cytoxicity profiles using the NcI anticancer drug screen and clustered image map visualizations. Crit. Revs. Oncol./Hematool. 53:25-34 (2005).) As stated, all modifications of transplatinum compounds reported to date are of the form trans-[PtCl$_2$(L)(L')] where L and L' are various amines other than NH$_3$. Unfortunately, these compounds are poorly soluble in aqueous medium and thus their in vivo bioavailability is attenuated. In addition, these known compounds still contain the relatively reactive Cl—Pt—Cl axis, making them unstable in the cellular environment. (McGowan, G.; Parsons, S.; Sadler, P. J., Inorg. Chem., 2005, 44, 7459-7467.)

There is therefore an ongoing need to develop new transplatinum compounds that are effective cytotoxic and antitumor agents. It would be particularly advantageous if the agents were water soluble, stable in the cellular environment, and cytotoxic and antitumor active in tumor cells that develop resistance to other known anti-tumor agents.

The following also are mentioned as background:

U.S. Pat. No. 4,979,393 issued Jan. 10, 1989 to N. Farrell et al., for "Bis-platinum complexes as chemotherapeutic agents."

U.S. Pat. No. 4,921,963 issued May 1, 1990 to Skov, Farrell, et al., for "Platinum complexes with one radiosensitizing ligand."

U.S. Pat. No. 5,026,694 issued Jun. 25, 1991 to Skov, Farrell, et al., for "Platinum complexes with one radiosensitizing ligand."

U.S. Pat. No. 5,028,726 issued Jul. 2, 1991, to Farrell for "Platinum amine sulfoxide complexes."

U.S. Pat. No. 5,107,007 issued Apr. 21, 1992 to Farrell for "Bis-platinum complexes as chemotherapeutic agents."

U.S. Pat. No. 5,380,897 issued Jan. 10, 1995 to Hoeschele, Qu and Farrell, for "Tri(platinum) complexes."

U.S. Pat. No. 5,409,915 issued Apr. 25, 1995 to Farrell et al., for "Bis-platinum (IV) complexes as chemotherapeutic agents."

U.S. Pat. No. 5,624,919 issued Apr. 29, 1997 to Farrell for "Trans-platinum (IV) complexes."

U.S. Pat. No. 5,744,497 issued Apr. 28, 1998 to Valsecchi, et al., including Farrell, for "Trinuclear cationic platinum complexes having antitumor activity and pharmaceutical compositions containing them."

U.S. Pat. No. 5,770,591 issued Jun. 23, 1998 to N. Farrell for "Bis-platinum complexes as chemotherapeutic agents."

U.S. Pat. No. 6,001,872 issued Dec. 14, 1999 to N. Farrell, et al., for "Water soluble transplatinum complexes with anti-cancer activity and method of using same."

U.S. Pat. No. 6,011,166 issued Jan. 4, 2000 to Valsecchi et al., including Farrell, for "Trinuclear cationic platinum complexes having antitumor activity and pharmaceutical compositions containing them."

U.S. Pat. No. 6,022,892 issued Feb. 8, 2000 to Farrell, et al., for "Bis-platinum complexes with polyamine ligands as antitumor agents."

U.S. Pat. No. 6,060,616 issued May 9, 2000 to Farrell, et al., for "Bis-platinum complexes with polymethylene derivatives as ligands having antitumor activity."

U.S. Pat. No. 6,113,934 issued Sep. 5, 2000 to Farrell, et al., for "Platinum complexes with anti-viral activity and method of using same."

U.S. Pat. No. 6,313,333 issued Nov. 6, 2001 to Da Re, et al., including Farrell, for "Multinuclear cationic platinum complexes with antitumor activity."

U.S. Pat. No. 6,350,740 issued Feb. 26, 2002 to N. Farrell, for "Transplatinum complexes as cytotoxic and anticancer agents."

S. Radulovic, Z. Tesic and S. Manic, *Curr. Med. Chem.*, 2002, 9, 1611.

Y. Najajreh, J. M. Perez, C. Navarro-Ranninger and D. Gibson, *J. Med. Chem.*, 2002, 45, 5189.

J. Kasparkva, O. Novakova, V. Marini, Y. Najajreh, D. Gibson, J. M. Perez and V. Brabec, *J. Biol. Chem.*, 2003, 278, 47516.

J. Kasparkova, V. Marini, Y. Najajreh, D. Gibson and V. Brabec, *Biochemistry*, 2003, 42, 6312.

E. S. F. Ma, W. D. Bates, A. Edmunds, L. R. Kelland, T. Fojo and N. Farrell, *J. Med. Chem.*, 2005, 48, 5651.

U.S. Pat. No. 6,867,316 issued Mar. 15, 2005 to Sohn, et al., for "Platinum (II) complexes of N-substituted amino dicarboxylates and the preparation method thereof."

U.S. Pat. Application No. 20050090478 published Apr. 28, 2005 by Barenholz, et al., for "Platinum complexes and their use in cancer treatment."

S. Zutphen, E. Pantoja, R. Soriano, C. Soro, D. Tooke, A. Spek, H. Dulk, J. Brouwer, J. Reedijk, "New antitumour active platinum compounds containing carboxylate ligands in trans geometry: synthesis, crystal structure and biological activity, *Dalton Trans.*, 2006, 1020-1023, DOI: 10.1039/b512357g (web-published Dec. 7, 2005).

SUMMARY OF THE INVENTION

The present invention provides novel, water soluble, cytotoxic complexes. The complexes have a trans axis that enhances solubility, yet the complexes are relatively stable in an aqueous environment. The new Pt complexes exhibit high levels of cytotoxicity. Importantly, the complexes are highly toxic even in cells that have become resistant to killing by conventional Pt-based agents (e.g. cisplatin and oxaliplatin).

The invention in a preferred embodiment provides a trans-platinum II complex of formula trans-[Pt(carboxylato)$_2$(L)(L')] where carboxylato=a ligand derived from an anion of a carboxylic acid (such as, e.g., a carboxylato ligand that is, e.g., formate, acetate, hydroxyacetate, chloroacetate, trifluoroacetate and lactate including optical isomers thereof), and: wherein L and L' are both planar heterocyclic amines (such as, e.g., pyridine, substituted pyridines, quinoline, subsituted quinolines, isoquinoline, substituted isoquinolines, thiazole, and substituted thiazoles), or one of L or L' is a planar heterocyclic amine and the other is not a planar heterocyclic amine and is selected from the group consisting of: NH$_3$, a branched aliphatic amine, an iminoether, a primary amine, a secondary amine and an aliphatic nitrogen-containing heterocycle, such as, e.g., trans-platinum II complexes wherein both L and L' are planar amines; trans-platinum II complexes wherein L and L' include a planar amine and an aliphatic non-N-H$_3$ amine; trans-platinum II complexes wherein L is a planar amine and L' is NH$_3$; trans-platinum II complexes wherein the aliphatic nitrogen-containing heterocycle is selected from the group consisting of piperzine, piperidine and pyrazole; trans-platinum II complexes wherein the carboxylato groups are in trans position to each other and L and L' are in trans position to each other; trans-platinum II complexes having cytotoxicity to human tumor cells (such as, e.g., trans-platinum II complexes having cytotoxicity of at least 10 µM when measured using a standard testing methodology for cell growth inhibition such as the MTT assay); etc.

The invention in another preferred embodiment provides a trans-platinum II complex represented by formula (I) as follows:

wherein
i) RCOO— is a carboxylate anion of a carboxylic acid and R is H or an alkyl group which may be substituted or unsubstituted; and
  ii) L and L' are both planar heterocyclic amines (such as, e.g., pyridine, substituted pyridines, substituted quinolines, isoquinoline, substituted isoquinolines, thiazole, and substituted thiazoles), or
  one of L or L' is a planar heterocyclic amine and the other is selected from the group consisting of $NH_3$, a branched aliphatic amine, an iminoether, a primary amine, a secondary amine and an aliphatic nitrogen-containing heterocycle (such as, e.g.,piperazine, piperidine, pyrazole). L may be a substituent (such as, e.g., Me, Br, Cl, F).

Another embodiment of the invention provides a method of treating cancer in a patient, comprising: administering to the patient a pharmaceutically effective amount of a novel trans-platinum II complex above-mentioned.

The invention in another preferred embodiment provides a method of killing cancer cells, comprising: contacting cancer cells with a novel trans-platinum II complex above-mentioned.

Also in a preferred embodiment the invention provides a method of solubilizing a trans-platinum compound to be water soluble, comprising attaching at least one solubilizing agent to said compound, wherein the solubilizing agent comprises a first carboxylato group and a second carboxylato group positioned trans to one another in said compound, wherein the carboxylate groups are the same, such as, e.g., methods wherein said compound is a trans-platinum II complex of formula trans-[Pt(carboxylato)$_2$(L)(L')] where carboxylato=a ligand (e.g., formate, acetate, hydroxyacetate, chloroacetate, trifluoroacetate and lactate including optical isomers thereof) derived from an anion of a carboxylic acid, and wherein L and L' are both planar heterocyclic amines (e.g., pyridine, substituted pyridines, substituted quinolines, isoquinoline, substituted isoquinolines, thiazole, and substituted thiazoles), or one of L or L' is a planar heterocyclic amine and the other cannot be a planar heterocylic amine and is selected from the group consisting of: $NH_3$, a branched aliphatic amine, an iminoether, a primary amine, a secondary amine and an aliphatic-containing heterocycle (e.g., piperazine, piperidine, pyrazole).

The invention in another preferred embodiment provides a method of synthesizing a trans-platinum II complex, comprising at least the steps of: converting a starting material selected from the group consisting of $K_2PtCl_4$ and cis-[PtCl$_2$(NH$_3$)$_2$] into an intermediate trans diido compound trans-[Pt I$_2$(L)(L')], wherein L is selected from the group consisting of pyridine, quinoline, isoquinoline and thiazole; L' is $NH_3$; followed by converting the intermediate trans diido compound into a trans-platinum II complex trans-[Pt(RCOO)$_2$(L)(NH$_3$)]; such as, e.g., synthesis methods including synthesis of a symmetric (L=L') trans platinum II complex from a starting material $K_2[PtCl_4]$; synthesis methods including synthesis of an unsymmetric (L and L' differ) trans platinum II complex from a starting material cis-[PtCl$_2$(L)$_2$] or cis-[PtCl$_2$(L')$_2$]; synthesis methods including reacting the starting material with L and L' to substitute the Pt with L and L', followed by a step of reacting the L, L' substituted Pt compound with H Cl to form a trans-[Pt(Cl)$_2$(L)(L')] compound, followed by a step of reacting the trans-[Pt(Cl)$_2$(L)(L')] compound with NaI in acetone or a solvent other than DMF to form the diido intermediate compound; synthesis methods including reacting the diiodo intermediate compound with Ag(RCOO) in acetone or a solvent other than DMF until trans-[Pt(RCOO)$_2$(L)(L')] is formed; synthesis methods including forming the trans platinum (II) complex from the starting material without using DMF in any step; etc.

In another preferred embodiment, the invention provides a method of synthesizing a trans-platinum II complex, comprising:
converting a starting material selected from the group consisting of $K_2[PtCl_4]$ and cis-[PtCl$_2$(NH$_3$)$_2$] into a trans-platinum IR complex trans-[Pt(RCOO)$_2$(L)(L')] without using DMF nor any high-boiling solvent with a boiling point in a range of DMF in any step; such as, e.g., synthesis methods including a step of forming a trans-[Pt(RCOO)$_2$(L)(L')] via a diido intermediate compound.

The invention in a further preferred embodiment provides a method of releasing a hydrolyzed trans-platinum compound comprising: selecting a carboxylato group for a desired rate of release associated with the carboxylato group for a hydrolyzed species of a trans-platinum compound; attaching at least two carboxylato groups trans to one another to the trans-platinum compound.

DETAILED DESCRIPTION OF THE PREFERRED EMBODIMENTS OF THE INVENTION

The present invention relates to new trans-platinum II complexes with cytotoxic activity. Significantly, these complexes are cytotoxic in tumor cells that are resistant to the toxic effects of traditional Pt-based anti-tumor drugs such as cisplatin and oxaliplatin. Without being bound by theory, it appears that, unlike the currently available platinum drugs, these complexes do not produce DNA damage by intrastrand cross-linking of base pairs. Instead, they may cause cell death by causing a set of structurally distinct DNA lesions including DNA-protein crosslinks. As a result, tumor cells that have developed resistance to known platinum drugs are still sensitive to these trans compounds. Current FDA approved platinum drugs include cisplatin, carboplatin and oxaliplatin, all of which have a cis geometry around the platinum atom. It is expected that these new trans compounds will complement existing chemotherapeutic agents, although they may also be used to kill any tumor cell, regardless of whether or not the tumor cell is resistant to classical Pt-based anti-tumor agents.

Remarkably, the complexes, which contain two carboxylate ligands in trans position, are very water soluble in comparison to the parent dichlorides, and yet are kinetically inert to hydrolysis and thus stable in an aqueous environment.

These compounds have the general formula trans [Pt(carboxylato)$_2$(L)(L')] where "carboxylato" is an anionic ligand derived from a carboxylic acid, for example, formate, acetate, hydroxyacetate, chloroacetate, trifluoroacetate, lactate, and the like; L is preferably a planar, aromatic amine like pyridine, quinoline, isoquinoline or thiazole; and L' can be NH$_3$ or the same amine as L. Other examples of L will also include aliphatic cyclic amines (such as cyclohexylamine, piperazine, piperidine), branched aliphatic amines and iminoethers. The compounds thus represent the first cytotoxic transplatinum compounds with N$_2$O$_2$ donor sets, similar to carboplatin and oxaliplatin.

Without being bound by theory, it is probable that the reactivity of these compounds is dictated mostly by the ability of the labile ligands (the carboxylato leaving groups) to be replaced by water producing aquated (hydrolysed) species, while the solubility is enhanced by the presence of a trans axis and the hydrophilicity of both the leaving group and the aromatic amine. The inclusion of polar groups in the ligands enhances the solubility while strong electronegative groups enhance the leaving group character.

The Pt(II) based complexes of the invention are schematically depicted in Formula I.

Herein, "planar heterocyclic amine" refers, e.g., to pyridine, substituted pyridines, substituted quinolines, isoquinoline, substituted isoquinolines, thiazole, and substituted thiazoles.

In "RCOO—" which has been mentioned for practicing the invention and is a carboxylate anion of a carboxylic acid, R is, for example, H, CH$_3$, or a straight or branched alkyl chain of from about 2 to about 5 carbons, and may be substituted or unsubstituted (e.g., with OH, Cl, F, Me, Br, etc., of which preferred substituents are Me, Br, Cl and F). In other words, the "OOCR" carboxylato moiety represents a carboxylic acid such as, for example, formate, acetate, hydroxyacetate, chloroacetate, trifluoroacetate, lactate (in the form of either optical isomer), etc. R may be substituted or unsubstituted.

An example of an inventive compound according to Formula I is a compound in which L is pyridine, quinoline or isoquinoline, or another N-donor ligand (e.g., cyclic aliphatic amines, linear and branched-chain alkyl amine and iminoethers) and L is not NH$_3$, and in which L' is pyridine, quinoline, isoquinoline or thiazole or an N-donor ligand (e.g., cyclic aliphatic amines, linear and branched-chain alkyl amine and iminoethers), or NH$_3$. L and L' may be the same OF different.

The invention also provides other trans-platinum (II) complexes, comprising: an N$_2$O$_2$ donor set, preferably trans-platinum (II) complexes wherein the N$_2$O$_2$ donor set comprises a donor (neutral) ligand N and a leaving (anionic) group O.

The invention also provides pharmaceutical compositions containing the compounds of formula I with pharmaceutically acceptable excipients. While the compounds can be administered in the pure form, more frequently they are administered in a pharmaceutically acceptable formulation including suitable elixirs, binders, and the like or as pharmaceutically acceptable salts or other derivatives. It should be understood that the pharmaceutically acceptable formulations and salts include liquid and solid materials conventionally utilized to prepare injectable dosage forms and solid dosage forms such as tablets and capsules. Water may be used for the preparation of injectable compositions which may also include conventional buffers and agents to render the injectable composition isotonic. Other potential additives include: colorants; surfactants (TWEEN, oleic acid, etc.); and binders or encapsulants (lactose, liposomes, etc). Solid diluents and excipients include lactose, starch, conventional disintergrating agents, coatings and the like. Preservatives such as methyl paraben or benzalkium chloride may also be used. Depending on the formulation, it is expected that the active composition will consist of 1-99% of the Pt complexes and the vehicular "carrier" will constitute 1-99% of the composition. The pharmaceutical compositions of the present invention may include any suitable pharmaceutically acceptable additives or adjuncts to the extent that they do not hinder or interfere with the therapeutic effect desired of the Pt complex.

The invention also provides a method of treating tumors which are susceptible to platinum complex treatment with one or more compounds of formula I. Implementation of the claimed method will generally involve identifying patients suffering from tumors and administering the platinum compound(s) in an acceptable form by an appropriate route. The dosage to be administered is usually determined in Phase I clinical trials and may vary depending on the age, gender, weight and overall health status of the individual patient, as well as the nature of the cancer itself, among other considerations. Administration can be oral or parenteral, including intravenously, intramuscularly, subcutaneously, etc., or by other routes (e.g. transdermal, sublingual, aerosol, etc.). The administration of pharmaceutical compositions of the present invention can be intermittent, or at a gradual or continuous, constant or controlled rate to a patient. In addition, the time of day and the number of times per day that the pharmaceutical formulation is administered can vary. Further, the effective dose can vary depending upon factors such as the mode of delivery, gender, age, and other conditions of the patient, as well as tumor type and stage or grade.

Generally, for parenteral administration in humans, dosages in the range of from about 0.1 to about 500 mg active Pt compound/kg body weight/24 hr., more preferably 1.0 to 20.0 active Pt compound/kg body weight/24 hr., are effective. The level of efficacy and optimal amount of dosage for any given Pt complex varies from complex to complex.

The Pt complexes of the present invention may be administered alone or in combination with other cancer therapies, e.g. other antitumor agents, radiation, etc. Since the compounds of the present invention are complementary to known anti-tumor cis-Pt compounds and are toxic to cancer cells that are resistant to known compounds, one strategy for cancer treatment is to use the drugs of the present invention in combination with traditional cis-Pt drugs. For example, administration of the two genres of drugs may be alternated in a patient, or even administered together. Alternatively, it may be desirable to wait until resistance to the conventional cis-Pt drugs is evident and then begin treatment with the novel trans-Pt drugs. Yet another alternative is to treat first with the trans-Pt drugs of the invention, and follow that treatment with conventional drugs if resistance to trans-Pt drugs develops. In addition, more than one of the novel Pt-complexes described herein may be administered to a patient, either separately, or in a single preparation. All such variations, as well as others that will occur to those of skill in the art, are encompassed by the methods of the present invention.

The invention further provides a process to prepare compounds of formula I. When L and L' are the same, the preparation generally involves the steps of reacting K$_2$PtCl$_4$ with excess nitrogen donor ligand, L, under conditions in which the ligand replaces the halogen ion of the salt to eventually form the cation [Pt(L)$_4$]$^{2+}$ which is then reacted in concentrated HCl under conditions in which trans-[PtCl$_2$(L$_2$)] is formed. The trans-[PtCl$_2$(L$_2$)] is then either:

1) preferably, reacted with excess NaI under conditions where I replace Cl, forming trans-[PtI$_2$(L$_2$)] and the trans-[PtI$_2$(L$_2$)] subsequently reacted with Ag(RCOO) under conditions in which I is replaced by RCOO to form trans-[Pt(COOR$_2$)(L$_2$)]; or
2) alternately, reacted with Ag(RCOO) under conditions in which Cl is is replaced by RCOO to form trans-[Pt(COOR$_2$)(L$_2$)].

In the case of 1) the critical trans-[PtI$_2$(L$_2$)] may also be prepared directly from the [Pt(L)$_4$]$^{2+}$ cation and I. When L and L' are not the same and L'=N$_3$, the procedure is the same except the starting material is cis-[Pt(Cl$_2$)(NH$_3$)$_2$] instead of K$_2$PtCl$_4$. When L and L' are not the same the procedure is the same except the starting material is cis-[Pt(Cl$_2$)(L)$_2$] or cis-[Pt(Cl$_2$)(L')$_2$] and the intermediate cation is [Pt(L)$_2$(L')$_2$]$^{2+}$ which is converted into trans-[PtI$_2$(L)(L')] as above. The synthesis of exemplary Pt II complexes of the invention is described in detail in Example 6 below.

Non-limiting examples of novel compounds according to this invention are as follows:

A trans-platinum(II) complex wherein the N$_2$O$_2$ donor set comprises a donor (neutral) ligand N and a leaving (anionic) carboxylato group O;

A trans-platinum(II) complex of formula trans-[Pt(carboxylato)$_2$(L)(L')] where carboxylato=an anionic ligand of a carboxylic acid (with examples of L being, e.g., a planar amine; an aliphatic cyclic amine (such as, e.g., cyclohexylamine; piperazine, piperidine (which may be substituted or unsubstituted); etc.); a branched aliphatic amine; an iminoether; etc.);

A trans-platinum (II) complex including a carboxylato acid ligand selected from the group consisting of formate, acetate, hydroxyacetate, chloroacetate, trifluoroacetate and lactate (in either optical isomeric form of lactate);

A trans-platinum (II) complex comprising two carboxylato groups disposed in trans position from each other about a platinum atom, wherein the two carboxylato groups are the same;

A trans-platinum(II) complex represented by a formula trans-[PtX$_2$(L)(L')] wherein the X groups are in trans position from each other and L and L' are in trans position from each other, X is an anion of a carboxylic acid; L and L' (which may be the same or different) together form an N$_2$O$_2$ donor set in which L is a heterocyclic aromatic amine or an N-donor ligand other than NH$_3$ and L' is a heterocyclic aromatic amine or an N-donor ligand and may include NH$_3$.

Some exemplary inventive compounds include, e.g., the following, by way of non-limiting limiting examples:

trans-[Pt(OAc)$_2$(NH$_3$)(py)] (trans-[diacetato(ammine)(pyridine)platinum(II)]);
trans-[Pt(OAc)$_2$(NH$_3$)(2Me-py)] (trans-[diacetato(ammine)(2-methylpyridine)platinum(II)]);
trans-[Pt(OAc)$_2$(NH$_3$)(3Me-py)] (trans-[diacetato(ammine)(3-methylpyridine)platinum(II)]);
trans-[Pt(OAc)$_2$(NH$_3$)(4Me-py)] (trans-[diacetato(ammine)(4-methylpyridine)platinum(II)]);
trans-[Pt(OAc)$_2$(NH$_3$)(tz)] (trans-[diacetato(ammine)(thiazole)platinum(II)]);
trans-[Pt(OAc)$_2$(NH$_3$)(quin)] (trans-[diacetato(ammine)(quinoline)platinum(II)]);
trans-[Pt(OAc)$_2$(NH$_3$)(Iq)] (trans-[diacetato(ammine)(isoquinoline)platinum(II)]);
trans-[Pt(OFm)$_2$(NH$_3$)(py)] (trans-[diformato(ammine)(pyridine)platinum(II)]);
trans-[Pt(OFm)$_2$(NH$_3$)(2Me-py)] (trans-[diformato(ammine)(2-methylpyridine)platinum(II)]);
trans-[Pt(OFm)$_2$(NH$_3$)(3Me-py)] (trans-[diformato(ammine)(3-methylpyridine)platinum(II)]);
trans-[Pt(OFm)$_2$(NH$_3$)(4Me-py)] (trans-[diformato(ammine)(4-methylpyridine)platinum(II)]);
trans-[Pt(OFm)$_2$(NH$_3$)(tz)] (trans-[diformato(ammine)(thiazole)platinum(II)]);
trans-[Pt(OFm)$_2$(NH$_3$)(quin)] (trans-[diformato(ammine)(quinoline)platinum(II)]);
trans-[Pt(OFm)$_2$(NH$_3$)(Iq)] (trans-[diformato(ammine)(isoquinoline)platinum(II)]);
trans-[Pt(lact)$_2$(NH$_3$)(py)] (trans-[dilactato(ammine)(pyridine)platinum(II)]);
trans-[Pt(lact)$_2$(NH$_3$)(2Me-py)] (trans-[dilactato(ammine)(2-methylpyridine)platinum(II)]);
trans-[Pt(lact)$_2$(NH$_3$)(3Me-py)] (trans-[dilactato(ammine)(3-methylpyridine)platinum(II)]);
trans-[Pt(lact)$_2$(NH$_3$)(4Me-py)] (trans-[dilactato(ammine)(4-methylpyridine)platinum(II)]);
trans-[Pt(lact)$_2$(NH$_3$)(tz)] (trans-[dilactato(ammine)(thiazole)platinum(II)]);
trans-[Pt(lact)$_2$(NH$_3$)(quin)] (trans-[dilactato(ammine)(quinoline)platinum(II)]);
trans-[Pt(lact)$_2$(NH$_3$)(Iq)] (trans-[dilactato(ammine)(isoquinoline)platinum(II)]);
trans-[Pt(OAcOH)$_2$(NH$_3$)(py)] (trans-[dihydroxyacetato(ammine)(pyridine)platinum(II)]);
trans-[Pt(OAcOH)$_2$(NH$_3$)(2Me-py)] (trans-[dihydroxyacetato(ammine)(2-methylpyridine)platinum(II)]);
trans-[Pt(OAcOH)$_2$(NH$_3$)(3Me-py)] (trans-[dihydroxyacetato(ammine)(3-methylpyridine)platinum(II)]);
trans-[Pt(OAcOH)$_2$(NH$_3$)(4Me-py)] (trans-[dihydroxyacetato(ammine)(4-methylpyridine)platinum(II)]);
trans-[Pt(OAcOH)$_2$(NH$_3$)(tz)] (trans-[dihydroxyacetato(ammine)(thiazole)platinum(II)]);
trans-[Pt(OAcOH)$_2$(NH$_3$)(quin)] (trans-[dihydroxyacetato(ammine)(quinoline)platinum(II)]);
trans-[Pt(OAcOH)$_2$(NH$_3$)(Iq)] (trans-[dihydroxyacetato(ammine)(isoquinoline)platinum(II)]);
trans-[Pt(TFA)$_2$(NH$_3$)(py)] (trans-[bis(trifluoro)acetato(ammine)(pyridine)platinum(II)]);
trans-[Pt(TFA)$_2$(NH$_3$)(2Me-py)] (trans-[bis(trifluoro)acetato(ammine)(2-methylpyridine)platinum(II)]);
trans-[Pt(TFA)$_2$(NH$_3$)(3Me-py)] (trans-[bis(trifluoro)acetato(ammine)(3-methylpyridine)platinum(II)]);
trans-[Pt(TFA)$_2$(NH$_3$)(4Me-py)] (trans-[bis(trifluoro)acetato(ammine)(4-methylpyridine)platinum(II)]);
trans-[Pt(TFA)$_2$(NH$_3$)(py)] (trans-[bis(trifluoro)acetato(ammine)(thiazole)platinum(II)]);
trans-[Pt(TFA)$_2$(NH$_3$)(quin)] (trans-[bis(trifluoro)acetato(ammine)(quinoline)platinum(II)]);
trans-[Pt(TFA)$_2$(NH$_3$)(Iq)] (trans-[bis(trifluoro)acetato(ammine)(isoquinoline)platinum(II)]);
trans-[Pt(OAc)$_2$(py)$_2$] (trans-[diacetatobis(pyridine)platinum(II)]);
trans-[Pt(OAc)$_2$(2Me-py)$_2$] (trans-[diacetatobis(2-methylpyridine)platinum(II)]);
trans-[Pt(OAc)$_2$(3Me-py)$_2$] (trans-[diacetatobis(3-methylpyridine)platinum(II)]);
trans-[Pt(OAc)$_2$(4Me-py)$_2$] (trans-[diacetatobis(4-methylpyridine)platinum(II)]);
trans-[Pt(OAc)$_2$(tz)$_2$] (trans-[diacetatobis(thiazole)platinum(II)]);
trans-[Pt(OFm)$_2$(py)$_2$] (trans-[diformatobis(pyridine)platinum(II)]);
trans-[Pt(OFm)$_2$(2Me-py)$_2$] (trans-[diformatobis(2-methylpyridine)platinum(II)]);

trans-[Pt(OFm)$_2$(3Me-py)$_2$] (trans-[diformatobis(3-methylpyridine)platinum(II)]);
trans-[Pt(OFm)$_2$(4Me-py)$_2$] (trans-[diformatobis(4-methylpyridine)platinum(II)]);
trans-[Pt(OFm)$_2$(tz)$_2$] (trans-[diformatobis(thiazole)platinum(II)]);
trans-[Pt(lact)$_2$(py)$_2$] (trans-[dilactatobis(pyridine)platinum(II)]);
trans-[Pt(lact)$_2$(2Me-py)$_2$] (trans-[dilactatobis(2-methylpyridine)platinum(II)]);
trans-[Pt(lact)$_2$(3Me-py)$_2$] (trans-[dilactatobis(3-methylpyridine)platinum(II)]);
trans-[Pt(lact)$_2$(tz)$_2$] (trans-[dilactatobis(thiazole)platinum(II)]);
trans-[Pt(OAcOH)$_2$(py)$_2$] (trans-[dihydroxyacetatobis(pyridine)platinum(II)]);
trans-[Pt(OAcOH)$_2$(2Me-PY)$_2$] (trans-[dihydroxyacetatobis(2-methylpyridine)platinum(II)]);

Novel trans-platinum II complexes having cytotoxicity to human tumor cells are preferred, such as trans-platinum II complexes having cytotoxicity measured of at least 10 μM when measured using a MTT assay or other standard testing methodology for cell growth inhibition.

EXAMPLES

Examples 1-4

Synthesis of Trans-platinum compounds of general formula trans-[Pt(carboxylato)$_2$(L)(L')]

The synthesis of trans-platinum compounds of general formula trans Pt(carboxylato)$_2$(L)(L') is shown in Scheme 1. A general synthetic procedure was developed that would lead to either symmetric or unsymmetric complexes depending on the starting Scheme 1.

trans-[Pt(OAcOH)$_2$(3Me-PY)$_2$] (trans-[dihydroxyacetatobis(3-methylpyridine)platinum(II)]);
trans-[Pt(OAcOH)$_2$(4Me-py)$_2$] (trans-[dihydroxyacetatobis(4-methylpyridine)platinum(II)]);
trans-[Pt(OAcOH)$_2$(tz)$_2$] (trans-[dihydroxyacetatobis(thiazole)platinum(II)]);
trans-[Pt(TFA)$_2$(py)$_2$] (trans-[bis(trifluoro)acetatobis(pyridine)platinum(II)]);
trans-[Pt(TFA)$_2$(2Me-py)$_2$] (trans-[bis(trifluoro)acetatobis(2-methylpyridine)platinum(II)]);
trans-[Pt(TFA)$_2$(3Me-py)$_2$] (trans-[bis(trifluoro)acetatobis(3-methylpyridine)platinum(II)]);
trans-[Pt(TFA)$_2$(4Me-py)$_2$] (trans-[bis(trifluoro)acetatobis(4-methylpyridine)platinum(II)]);
trans-[Pt(TFA)$_2$(tz)$_2$] (trans-[bis(trifluoro)acetatobis(thiazole)platinum(II)]),
with the following definitions applying to the above compounds: OAc=acetate $CH_3COO^-$;
OFm=formate $HCOO^-$; Lact=lactate $CH_3C^*H(OH)COO^-$ (*=R or S chirality); OAcOH=hydroxyacetate $HOCH_2COO^-$; TFA=trifluoroacetate $CF_3COO^1$; py=pyridine; 2Me-py=2-methylpyridine; 3Me-py=3-methylpyridine; 4Me-py=4-methylpyridine; tz=thiazole; Iq=isoquinoline; and quin=quinoline.

that would lead to either symmetric or unsymmetric complexes depending on the starting material. When a symmetric compound is desired, the starting reagent used is $K_2$ PtCl$_4$, and when a non-symmetric compound is required the starting reagent is cis-DDP, cis-Pt(NH$_3$)$_2$ Cl$_2$.

A suspension or solution of the starting platinum reagent in water is reacted with an excess of the aromatic amine, L, under reflux for 1.5 hr. The solution is removed from heat, activated charcoal is added, and the mixture is stirred for 10 min. After the solution is filtered, excess concentrated HCl is added and the mixture heated under reflux for 6 hr during which time a yellow precipitate is formed. After cooling the mixture overnight, the yellow product is filtered, washed with water, ethanol, and ethyl ether, and dried in vacuo. The product, trans-[PtCl$_2$LL'] can then be dissolved in DMF with warming and added to a mixture of 2.1 equiv. of the silver salt of the carboxylic acid in H2O. The mixture is stirred in the dark at 50° C. for 2 days. The precipitate of AgCl is filtered off and the filtrate is evaporated to dryness under vacuum. The residue is redissolved in hot methanol and left to crystallize.

A modification of this procedure involves the activation of the leaving groups in the precursor trans-[PtCl$_2$LL'] by replacing the chloride atoms with iodide atoms. Higher yields and cleaner products can sometimes be obtained using this approach. If activation is desired, the compound is suspended in a solution of excess NaI in acetone and the mixture stirred a room temperature overnight. NaCl is filtered off and the filtrate evaporated to dryness. The residue, trans-[PtI$_2$LL'] is washed with warm H$_2$O. methanol and ethyl ether and dried in vacuo. This compound is dissolved or suspended in acetone and added to 2.1 equiv. of the silver salt of the appropriate carboxylate. The mixture is stirred in the dark at 40-50° C. for 24 hr. AgI is filtered off through a pad of celite and the filtrate is concentrated until a white precipitate starts to appear at which point the mixture is placed in the fridge for a few hours. The precipitate is filtered, washed with ethyl ether, and dried in vacuo. The product usually can be recrystallized from methanol.

Silver salts of small, water soluble carboxylic acids can be prepared by reacting excess of the carboxylic acid with a suspension of silver carbonate or silver oxide in water. The mixture is stirred for 2 h in the dark at room temperature. The solution is filtered, concentrated until a precipitate appears and stored in the fridge to crystallize. The crystals are filtered, washed with cold water, and dried in vacuo in the dark. A second crop can be obtained when the filtrate is further concentrated.

Example 1 trans-PtCl$_2$(py)$_2$ Synthesis

A solution of 2.00 g (4.81 mmol) of K$_2$PtCl$_4$ and 6.00 mL (74.2 mmol) of pyridine in 160 mL of water was stirred at reflux. After 1 h, 10 mL of concentrated HCl were added to the solution and heating was continued for 5 h. After the mixture is stored at 4 °C. for 12 h, the light yellow precipitate was filtered off, washed with hot water, ethanol and diethyl ether, and finally dried in vacuo. Yield: 1.95 g (95%). $^1$H NMR in DMSO-d6: 8.79 ppm (2H d), 8.02 ppm (1H dt), 7.54 ppm (2H t).

Example 2 trans-[Pt(OAcOH)$_2$(py)$_2$] Synthesis trans-PtCl$_2$(py)2, 400 mg, 0.943 mmol, was dissolved in 20 mL DMF by warming to 50° C. with stirring. Silver hydroxyacetate, 345 mg, 1.89 mmol was dissolved in 20 mL of warm water and added to the yellow solution of trans-PtCl$_2$(py)$_2$. The mixture was heated to 50° C. and stirring continued in the dark for 2 days. The mixture was filtered to give a yellow solution and evaporated to dryness to give 488 mg of a yellow residue. The residue was dissolved almost completely in methanol and the material that remained undissolved was filtered off. The filtrate was concentrated and placed in the fridge to crystallize. Yield: 147 mg (31%). Anal. Calcd. for C$_{14}$H$_{16}$N$_2$O$_6$Pt: % C, 33.41; % H, 3.20; % N, 5.57. Found: % C, 33.25; % H 2.89; % N, 5.52. $^1$H NMR in D$_2$O: 8.514 ppm (2H d), 7.995 ppm (1H tt), 7.514 ppm (2H t), 4.020 ppm (2H s). $^{195}$Pt NMR in D$_2$O: −1459 ppm.

Example 3 trans-[Pt(OAc)$_2$(NH$_3$)(iquin)] Synthesis

AgOAc (700 mg, 4.19 mmol) was added to a solution of trans-[PtI$_2$(NH$_3$)(iquin)] (1.0 g, 1.68 mmol) in 225 mL acetone. After the mixture was stirred in the dark for 24 h at ambient temperature, 300 mL of acetone was added. The reaction mixture was heated to reflux for 15 min until the product dissolved dissolved. AgI and unreacted AgOAc were filtered off through a pad of Celite while still hot. The clear and colorless filtrate was concentrated to 50 mL and placed in the fridge (5° C.) for 20 h giving a off-white precipitate. The product was filtered off, washed with Et$_2$O (2×10 mL) and dried in vacuo. The product, which may contain minute amounts of Ag species, was recrystallized from acetone (100 mg/60 mL). Yield: 0.585 g (76%). Anal. Calcd for C$_{13}$H$_{16}$N$_2$O$_4$Pt.H$_2$O: C, 32.71;

H, 3.80; N, 5.87. Found: C, 32.44; H, 3.41; N, 5.75. $^1$H NMR in D$_2$O: 9.14 ppm (1H s), 8.24 ppm (1H d), 8.11 ppm (1H d), 7.98 ppm (1H d), 7.90 ppm (1H t), 7.84 ppm (1H d), 7.76 ppm (1H t), 1.96 ppm (6H s). $^{195}$Pt NMR in D$_2$O:1430 ppm.

Example 4 trans-[Pt(OAc)$_2$(NH$_3$)(iquin)] Synthesis

A suspension of AgOAc (162 mg, 0.97 mmol) in 12 mL H$_2$O which has been heated at 60° C. for 10 min in the dark is added to a solution of trans-[PtCl$_2$(NH$_3$)(iquin)] (200 mg, 0.49 mmol) in 10 mL DMF. The mixture is stirred in the dark at 50° C. for 2 days. AgCl is filtered off through a pad of Celite and washed with MeOH. The combined yellow filtrates are evaporated to dryness under vacuum and the yellow residue is redissolved in MeOH (15 mL). The yellow solution is treated with activated charcoal (200 mg) for 30 min. The mixture is passed through a new pad of Celite and the pale yellow filtrate is evaporated to dryness. The residue is redissolved in minimal MeOH (5 mL) with slight heating (60° C.). The solution is stored at 5° C. for 3 h during which time pale yellow crystals formed. The product is filtered off, washed with Et$_2$O (10 mL) and dried in vacuo. Yield: 50% pale yellow solid. Anal. Calcd. for C$_{13}$H$_{16}$N$_2$O$_4$Pt.(H$_2$O): % C, 32.71; % H, 3.80; % N 5.87. Found: % C, 32.44; % H, 3.42; % N, 5.75. $^1$H NMR in D$_2$O: 9.14 ppm (1H s), 8.24 ppm (1H d), 8.11 ppm (1H d), 7.98 ppm (1H d), 7.90 ppm (1H t), 7.84 ppm (1H d), 7.76 ppm (1H t), 1.96 ppm (6H s). $^{195}$Pt NMR in D$_2$O: −1429 ppm.

Using the previous methods, the following selected compounds were also prepared:

t-[Pt(OAcOH)$_2$(py)$_2$], Anal. Calcd. for C$_{14}$H$_{16}$N$_2$O$_6$Pt: C, 33.41; H, 3.20; N, 5.57. Found: C, 33.25; H 2.89; N, 5.52. $^{195}$Pt NMR in D$_2$O: −1459 ppm. $^1$H NMR in D$_2$O: 8.514 ppm (2H d), 7.995 ppm (1H tt), 7.514 ppm (2H t), 4.020 ppm (2H s).

t-[Pt(lactate)$_2$(py)$_2$], Anal. Calcd. for C$_{16}$H$_{20}$N$_2$O$_6$Pt: C, 36.16; H, 3.79; N, 5.27. Found: C, 36.20; H, 3.49; N, 5.20. $^1$H NMR in D$_2$O: 8.51 ppm (2H bd), 8.00 ppm (1H tt), 7.52 ppm (2H bt), 4.18 ppm (1H q), 1.11 ppm (3H d). $^{195}$Pt NMR in D$_2$O: −1481 ppm.

t-[Pt(CF$_3$COO)$_2$(py)$_2$], Anal. Calcd. for C$_{14}$H$_{10}$F$_6$N$_2$O$_4$Pt: C, 29.03; H, 1.74; N, 4.84. Found: C, 28.95; H, 1.38; N, 4.78. $^{195}$Pt NMR in CD$_3$OD: −1431 ppm. $^1$H NMR in CD$_3$OD: 8.651 ppm (2H bd), 8.042 ppm (1H tt), 7.582 ppm (2H bt). $^{19}$F NMR in CD$_3$OD: −76.39 ppm.

t-[Pt(CH$_2$ClCOO)$_2$(py)$_2$], Anal. Calcd. for C$_{14}$H$_{14}$Cl$_2$N$_2$O$_4$Pt: C, 31.12; H, 2.61; N, 5.19. Found: C, 31.26; H, 2.40; N, 5.08. $^1$H NMR in DMSO-d6: 8.57 ppm.(2H bd), 8.05 ppm (1H tt), 7.57 ppm (2H bt), 4.06 ppm (2H s).

t-[Pt(NH$_3$)(lactato)$_2$(Iq)], Anal. Calcd. for C$_{15}$H$_{20}$N$_2$O$_6$Pt: C, 34.69; H, 3.88; N, 5.39. Found: C, 33.23; H, 3.55; N, 5.18. $^1$H NMR in D$_2$O: 9.15 ppm (1H s), 8.24 ppm (1H d), 8.125 ppm (2H s), 7.98 ppm (1H s), 7.91 ppm (1H t), 7.86 ppm (1H d), 7.77 ppm (1H t), 4.23 ppm (2H q), 1.17 ppm (3H d). $^{195}$Pt NMR in $D_2O$: −1466 ppm.

t-[Pt(NH$_3$)(HCOO)$_2$(Iq)], Anal. Calcd. for $C_{11}H_{12}N_2O_4$Pt: C, 30.63; H, 2.80; N, 6.50. Found: C, 29.46; H, 3.04; N, 6.23. $^1$H NMR in $D_2O$: 9.18 ppm (1H s), 8.26 ppm (1H d), 8.11 ppm (1H d), 7.98 ppm (1H d), 7.90 ppm (1H t), 7.84 ppm (1H d), 7.77 ppm (1H t), 7.43 ppm (2H s). $^{195}$Pt NMR in $D_2O$: −1450 ppm.

Example 5

Enhancement of Aqueous Solubility and Stability Employing a Trans Acetate Axis in Transplanar Amine Platinum Compounds while Maintaining the Biological Profile

Background/Comparative Examples

Since the discovery of its anticancer activity cisplatin (cis-[PtCl$_2$(NH$_3$)$_2$], cis-DDP) has developed into a mainstay of many chemotherapeutic regimens.[1,2,3] The structure-activity relationships (SARs) developed since the introduction of cisplatin into the clinic emphasized the necessity for leaving groups having a cis geometry and an overall neutral charge on the Pt agent. Although many permutations based on this chemotype (cis-[Pt(amine)$_2$X$_2$], neutral Pt entities) have been explored, to date only carboplatin (cis-[Pt(CBDCA)(NH$_3$)$_2$], (CBDCA=cyclobutane-1,1-dicarboxylate) and oxaliplatin ([Pt(ox)(dach)]) (dach=1,2-diaminocyclohexane, ox=oxalato) have gained world-wide acceptance in the clinic.[4]

The principal factors affecting platinum complex cytotoxicity, valid for both inherent and acquired resistance, are (a) cellular uptake and efflux; (b) the nature and structure of target Pt-DNA adducts and (c) the extent of metabolizing reactions with sulfur nucleophiles, generally considered to be deactivating. One approach to expand the anticancer spectrum of platinum agents has been to examine structurally unique platinum agents with the hypothesis that novel Pt-DNA adducts not accessible to cisplatin may result in a differential cellular response.[5] One such class is represented by polynuclear platinum compounds, as exemplified by the trinuclear BBR3464, where the results of Phase II clinical trials showed partial responses in cisplatin-relapsed ovarian cancer.[6,7] A second approach has been to explore the trans geometry.[8,9] The paradigm for the early SARs was that the trans geometry, trans-[PtCl$_2$(NH$_3$)$_2$] (trans-DDP), was therapeutically inactive. A number of factors may contribute to this difference between simple geometric isomers. The trans isomer is kinetically more reactive than the cis isomer which may contribute to its deactivation. In addition, the primary toxic lesion in DNA formed by cis-DDP, a 1,2-intrastrand cross-link between adjacent GG base pairs, is sterically inaccessible to the trans isomer. The minor interstrand crosslink formed by cis-DDP is between adjacent GG base pairs in (GC) sequences.[10,11] In contrast, the trans isomer forms a unique 1,1-interstrand cross-link between GN7 and CN3 of the same GC base pair, a lesion distinctly less distorting to DNA structure than the cis case.[12] Protein recognition of both types of crosslink, and the biological consequences thereof, is likely to be significantly different between the two isomers.[13,14]

Substitution of the NH$_3$ group by a sterically hindered planar amine trans-[PtCl$_2$(L)(L')] (L=NH$_3$, L'=pyridine, quinoline, thiazole, etc. and/or L=L'=pyridine or thiazole) gives transplanaramine (TPA) compounds with cytotoxicity comparable to cisplatin in human tumor cell lines.[15,16] Use of the planar amine enhances cytotoxicity up to 100-fold over trans-[PtCl$_2$(NH$_3$)$_2$]. Further, the compounds generally maintain cytotoxicity in cisplatin-resistant lines. Since our initial reports, a number of other groups have confirmed the effects of a sterically demanding group in modulation of the cytotoxicity of the transplatinum structure—amines used include cyclohexylamine,[17] branched aliphatic amines,[18] piperazine, piperidine[19,20] and iminoethers.[9] In general the cytotoxicity of these various compounds is in the 1-20 μM range and is characterized by lack of cross-resistance to cisplatin. The DNA binding profiles of these various compounds show a wide diversity in comparison to those of the cisplatin family[21] and it is important to examine the chemistry and profile of DNA binding of these new transplatinum compounds and place them in context.

Despite the wide variation of amine carrier ligands, there has been little in vivo antitumor activity reported thus far for the transplatinum geometry.[8,22]

All previously-reported modifications of transplatinum compounds are of the form trans-[PtCl$_2$(L)(L')] where L and L' are various amines other than NH$_3$. These comparative compounds are poorly soluble in aqueous medium and still contain the relatively reactive Cl—Pt—Cl axis. To address the poor solubility of the comparative compounds, complexes were examined wherein a trans axis that enhances aqueous solubility is utilized. One approach was to develop trans-Pt compounds containing a planar amine chelating moiety (such as [SP-4-2]-[PtCl(NH$_3$)(pyOAc—N,O)] where pyOAc is 2-pyridylacetate).[23] More recent work led to the re-examination of whether the chelating function is necessary because the acetate group appears to not only enhance aqueous solubility but also slow down the rate of hydrolysis in these water-soluble TPA derivatives.[24]

Inventive Example 5

This present invention provides new, representative TPA compounds containing the acetate ligands as leaving groups in the trans axis. Use of acetate ligands (and carboxylate ligands in general) results in aqueous solubility and hydrolysis rates which leads to more desirable behavior in vivo. In addition, the biological profiles for these trans acetates indicate a lack of cross-resistance (collateral sensitivity) in tumor cells resistant to either cisplatin or oxaliplatin. The TPA-acetate derivatives are significantly more cytotoxic in many cis-DDP-resistant cell-lines than in the parent cis-DDP-sensitive cell-lines, an encouraging and remarkable finding. This new series of compounds is the first example of an N$_2$O$_2$ donor set for cytotoxic transplatinum compounds. Further, the "trans-carboxylate" strategy is a general one, applicable to all donor ligands such as alicyclic amines, iminoethers and heterocyclic aliphatic amines such as piperazine and piperidine.

The general synthetic pathway is described in Example 6. The diiodo compounds are especially useful intermediates as they are precursors of nitrato compounds which were isolated in all cases for use as controls in chemical studies.[25,26] Further, the acetone solubility of the diiodo compounds precludes the need for use of high-boiling solvents such as DMF which are necessary to solubilize the sparingly soluble chlorides. Characterization of all representative compounds was by elemental analysis, UV/Vis and NMR spectroscopy. Purity was assessed by HPLC.[27] An X-ray crystal structure determination of trans-[Pt(OAc)$_2$(py)$_2$] also confirmed the proposed structure.

The aqueous solubility of the acetate compounds and the acid dissociation constants of the corresponding aqua species are given in Table 1. Use of acetates enhances aqueous solubility which is dependent on the exact nature of the donor ligands. The $pK_a$ values were determined by potentiometric titration of solutions of trans-$[Pt(H_2O)_2(L)(L')]^{2+}$ (formed by the dissolution of the isolated trans-$[Pt(NO_3)_2(L)(L')]$) with NaOH. The first $pK_a$ is significantly lower than that found for cisplatin ($pK_{a1}$=5.37).[28] There is little variation amongst the various planar ligands, a feature also noted in the series trans-$[PtCl_2(NH_3)(X\text{-pyr})]$ (X=2,3,4-Me).[30]

TABLE 1 trans-$[Pt(H_2O)_2(L)(L')]^{2+}$ $\underset{}{\overset{pKa_1}{\rightleftharpoons}}$ trans-$[Pt(H_2O)(OH)(L)(L')]^+$ trans-$[Pt(H_2O)(OH)(L)(L')]^+$ $\underset{}{\overset{pKa_2}{\rightleftharpoons}}$ trans-$[Pt(OH)_2(L)(L')]$ Physical Properties of TPA-(Acetate) and $pK_a$ Values of the Corresponding TPA Diaqua Complexes at Ambient Temperature[a]

| Complex | Solubility, mg/mL | $pK_{a1}$ | $pK_{a2}$ |
|---|---|---|---|
| trans-$[Pt(OAc)_2(NH_3)_2]$ | 21 | 4.0[b] | 7.08 |
| trans-$[Pt(OAc)_2(py)_2]$ | 15 | 3.87 | 6.7 |
| trans-$[Pt(OAc)_2(NH_3)(quin)]$ | 1.6 | 3.89 | 7.01 |
| trans-$[Pt(OAc)_2(NH_3)(iquin)]$ | 5.2 | 3.78 | 6.92 |

[a]pH titration curves were obtained from the potentiometric titrations of $10^{-3}$ M solutions of trans-$[Pt(OH_2)_2(L)(L')]$ (produced from the corresponding dinitrato compounds) by a standardized NaOH solution (9.5 × $10^{-4}$ M). Solubility was measured by sequential addition of water, agitation for 15 minutes until solution was no longer clear.
[b]Literature values 4.35 and 7.40 by NMR.[29]

For hydrolysis studies, $10^{-3}$ mM complex was dissolved in 1 mL of nanopure water. The pH values of the samples were controlled in regular intervals and readjusted if necessary by addition of $HNO_3$ (1 M, 0.1 M, 0.01 M) or NaOH (1 M, 0.1 M, 0.01 M). Aliquots of 20 µL were taken from the bulk solution for HPLC analysis. The overall scheme may be described as follows:

The aquated species were identified by comparison with the hydrolysis profile produced by the corresponding (labile) nitrate compounds. The rate constants for the first aquation step k1 are given in Table 2 and compared with other platinum complexes containing one or two labile ligands. The rate for the TPA acetates (approx. $10^{-7}$ s$^{-1}$) is significantly slower than those of Pt complexes containing chloro ligands ($10^{-5}$ s$^{-1}$). In particular, these rates are 2-3 orders of magnitude lower than that of transplatin itself. The rate of aquation tends toward that of carboplatin which in phosphate buffer at 310 K gave a hydrolysis rate of $7.2 \times 10^{-7}$ s$^{-1}$ (but in aqueous solution gives a barely measurable rate constant of <$5 \times 10^{-9}$ s$^{-1}$, which is modulated by the presence of buffer, nucleophile or acid). [31,32] No evidence for formation of Pt(TV) species during hydrolysis is detected under these conditions.[33]

TABLE 2

Comparison of Hydrolysis Rates of TPA Acetates and Other Platinum Compounds.

| Compound | $k_1$ s$^{-1}$ |
|---|---|
| trans-$[Pt(OAc)_2(py)_2]$ | (3.2 ± 0.3) × $10^{-7}$ |
| trans-$[Pt(OAc)_2(NH_3)(quin)]$ | (3.7 ± 0.1) × $10^{-7}$ |
| trans-$[Pt(OAc)_2(NH_3)(iquin)]$ | (7.4 ± 1.5) × $10^{-7}$ |
| Cisplatin[34] | 5.18 × $10^{-5}$ |
| Carboplatin[31,32] | <$10^{-8}$ |
| Transplatin[35] | 19 × $10^{-5}$ |
| $[PtCl(dien)]+$,[36] | (6.50 ± 0.13) × $10^{-5}$ |

The acetate group (and carboxylate group in general) is a weak ligand and has a low trans influence and trans effect. The lability of monofunctional carboxylate is greater than chloride. In cis-$[Pt(amine)_2(RCO_2)_2]$, as exemplified by cis-$[Pt(PrNH_2)_2(ClCH_2CO_2)_2]$, analysis of the kinetics of substitution by water of the first carboxylate ligand (rate constant=$4.38 \times 10^{-5}$ s$^{-1}$) suggested a strong cis labilising effect of the mutually cis carboxylates.[37] This effect is absent in $[Pt(dien)(RCO_2)]^+$.[38] These measured rate constants are significantly higher than that measured here for the trans geometry. Placing two weak carboxylate ligands in a mutually trans-axial position of a square-planar Pt(II) compound results in little driving force for ligand substitution. Thus, surprisingly, trans-carboxylates are significantly more inert than simple considerations of the monofunctional carboxylate would indicate.

The $IC_{50}$ values in an ovarian cancer cell line panel are given in Table 3. It is noteworthy that the acetate compounds maintain cytotoxicity with low resistance factors in all cases. The trans-$[Pt(OAc)_2(NH_3)_2]$ compound is also very water-soluble but the cytotoxicity of >100 µM confirms the requirement for a planar amine to enhance cytotoxicity in the trans geometry.

TABLE 3

Evaluation of TPA-Acetate Derivatives in Human Ovarian Cancer Cell Line Panel (96 h exposure)[a]

| Compound | A2780 RF | CH1 RF | 41M RF |
|---|---|---|---|
| cis-$[PtCl_2(NH_3)_2]$ |  | 0.1 | 1.4 |
|  |  | (6.7) | (6.1) |
| trans-$[Pt(OAc)_2(NH_3)(quin)]$ | 13.0 | 17.0 | 22.0 |
|  | (1.46) | (0.48) | (1.00) |
| trans-$[Pt(OAc)_2(NH_3)(iquin)]$ | 13.0 | 20.0 | 22.0 |
|  | (1.69) | (0.37) | (0.26) |
| trans-$[Pt(OAc)_2(py)_2]$ | 12.8 | 19.0 | 14.0 |
|  | (0.90) | (0.22) | (0.32) |

[a]$IC_{50}$ (concentration necessary to inhibit growth at 50%) in µM. Values in parentheses are resistant factors, [RF = ($IC_{50}$ Resistant)/($IC_{50}$ Sensitive)]. Assays performed as per ref.[16].

Figure 1:
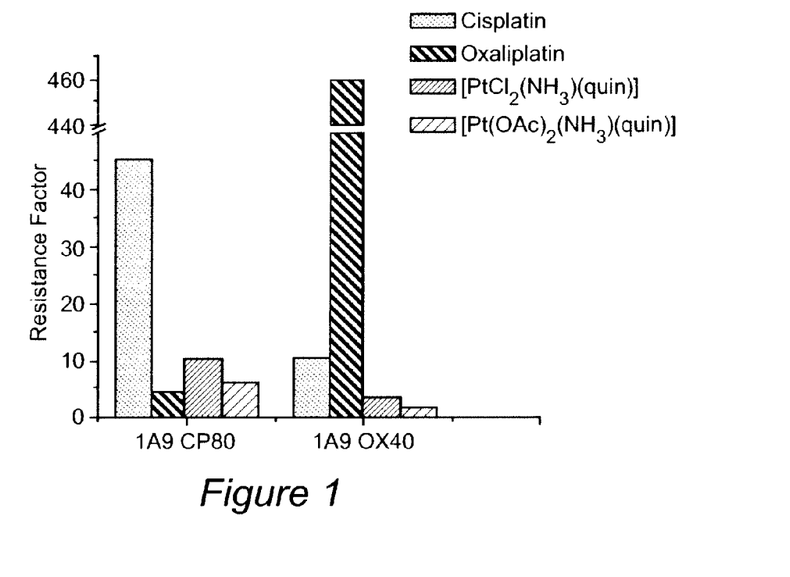
FIG. 1. Comparison of Resistance Factors of a representative isostructural TPA chloride and acetate complex in cisplatin and oxaliplatin-resistant (1AP CP80 and 1A9 OX40 respectively) ovarian tumor cell lines. Assays performed as per ref. 39 and 40.

A study of the cytotoxicity of the trans-$[PtCl_2(L)(L')]$ series across the NCI human tumor cell line panel showed a unique profile and activity in both cisplatin and oxaliplatin-resistant cells.[39] This property is maintained for the new acetate compounds and, indeed, resistance factors appear to be even lower than for the parent chlorides, as clearly seen in comparison of a representative compound in FIG. 1. Thus, the new compounds retain the desirable features of the parent compounds and the profile of cytotoxicity is similar.[39]

The chemistry of the new TPA acetate compounds described here is likely to affect all the principal pharmacological factors affecting platinum toxicity—cellular uptake, structure and nature of DNA lesions and the extent of deactivating metabolic interactions. In agreement, besides the expected profile of DNA binding,[8] cellular uptake is greatly enhanced for acetate compounds.⁴⁰ This combination of modulation of chemical properties may be reasonably expected to produce the cytotoxicity profile distinctly different from that of cisplatin and its congeners.

The compounds described here are the first transplatinum compounds containing an $N_2O_2$ donor set, similar to carboplatin and oxaliplatin. The reactivity of the new series suggests they are best considered as "carboplatin" analogs but in the trans geometry. The reactivity and aquation rates can be further modulated by variation of carboxylate ligand.⁴⁰ Carboplatin is significantly less potent than cisplatin in cell culture and is safely administered clinically at higher doses because of diminished side-effects. Application of this strategy to the diverse set of cytotoxic transplatinum compounds described in the literature could lead to the selection of clinical candidates with a profile genuinely different to that of the currently used agents.

References for Example 5

1. Platinum-Based Drugs in Cancer Therapy, Kelland, L. R. and Farrell, N. Eds., in "Cancer Drug Discovery and Development", Teicher, B. A., Ed. Humana Press (2000).
2. O'Dwyer, P. J.; Johnson, S. W.; Hamilton, T. C. Cisplatin and Its Analogues; 5 ed.; DeVita, V. T., Hellman, S. and Rosenberg, S. A., Ed.; Lippincott-Raven Publishers: Philadelphia, 1997; Vol. 2, pp 418-431.
3. Lippert, B, Cisplatin: Chemistry and biochemistry of a leading anticancer drug, Wiley-VCH, NY, 1999.
p0 4. Wong, E.; Giandomenico, C. M. Current Status of Platinum-Based Antitumor Drugs. Chem. Rev. 1999, 99, 2451-2466.
5. Farrell, N. Nonclassical platinum antitumor agents: perspectives for design and development of new drugs complementary to cisplatin. Cancer Invest. 1993, 11, 578-589.
6. Calvert, A. H.; Thomas, H.; Colombo, N.; Gore, M.; Earl, H.; Sena, L.; Camboni, G.; Liati, P.; Sessa, C. Phase II clinical study of BBR 3464, a novel, bifunctional platinum analogue, in patients with advanced ovarian cancer. Eur. J. Cancer 2001, 37(sup. 6) Poster 182.
7. Farrell, N. Polynuclear platinum drugs. Met. Ions Biol. Syst. 2004, 42, 251-296.
8. Farrell, N. Current status of structure-activity relationships of platinum anticancer drugs: activation of the trans geometry. Met. Ions Biol. Syst. 1996, 32, 251-296.
9. Intini, F. P.; Boccarelli, A; Francia, V. C.; Pacifico, C.; Sivo, M. F.; Natile, G.; Giordano, D; Rinaldis, P.; Coluccia, M. Platinum complexes with imino ethers or cyclic ligands mimicking imino ethers: synthesis, in vitro antitumour activity, and DNA interaction properties. J. Biol. Inorg. Chem. 2004, 9, 768-780.
10. Coste, F.; Malinge, J. M.; Serre, L.; Shepard, W.; Roth, M.; Leng, M.; Zelwer, C. Crystal structure of a double-stranded DNA containing a cisplatin interstrand cross-link at 1.63 A resolution: hydration at the platinated site. Nucleic Acids Res. 1999, 27, 1837-1846.
11. Huang, H.; Zhu, L.; Reid, B. R.; Drobny, G. P.; Hopkins, P. B. Solution structure of a cisplatin-induced DNA interstrand cross-link. Science 1995, 270, 1842-1845.
12. Brabec, V.; Leng, M. DNA interstrand cross-links of trans-diaminedichloroplatinum(II) are preferentially formed between guanine and complementary cytosine residues. Proc. Natl. Acad. Sci. U.S.A. 1993, 90, 5345-5349
13. Kartalou, M.; Essigmann, J. M. Recognition of cisplatin adducts by cellular proteins. Mutat. Res. 2001, 478, 1-21.
14. Jamieson, E. R.; Lippard, S. J. Structure, recognition, and processing of cisplatin-DNA adducts. Chem. Revs, 1999, 99, 2467-2498.
15. van Beusichem, M.; Farrell, N. Activation of the trans geometry in platinum antitumor complexes. Synthesis, characterization, and biological activity of complexes with the planar ligands pyridine, N-methylimidazole, thiazole, and quinoline. Crystal and molecular structure of trans-dichlorobis(thiazole)platinum(II). Inorg. Chem. 1992, 31, 634-639.
16. Farrell, N.; Kelland, L. R.; Roberts, J. D.; van Beusichem, M. Activation of the trans geometry in platinum antitumor complexes: a survey of the cytotoxicity of trans complexes containing planar ligands in murine L1210 and human tumor panels and studies on their mechanism of action. Cancer Res., 1992, 52, 5056-5072.
17. Mellish, K. J.; Barnard, C. F. J.; Murrer, B. A.; Kelland, L. R. DNA-binding properties of novel cis- and trans-platinum-based anticancer agents in 2 human ovarian carcinoma cell lines. Int. J. Cancer, 1995, 62, 717-723.
18. Montero, E. I.; Diaz, S.; Gonzalez-Vadillo, A. M.; Perez, J. M.; Alonso, C.; Navarro-Ranninger, C. Preparation and Characterization of Novel trans-[PtCl2(amine)(isopropylamine)] Compounds: Cytotoxic Activity and Apoptosis Induction in ras-Transformed Cells. J. Med. Chem. 1999, 42, 4264-4268.
19. Khazanov E.; Barenholz Y.; Gibson D.; Najajreh Y. Novel apoptosis-inducing trans-platinum piperidine derivatives: synthesis and biological characterization. J. Med. Chem. 2002, 45, 5196-204.
20. Najajreh Y.; Perez J. M.; Navarro-Ranninger, C.; Gibson, D. Novel soluble cationic trans-diaminedichloroplatinum (II) complexes that are active against cisplatin resistant ovarian cancer cell lines. J. Med. Chem. 2002, 45, 5189-95.
21. Brabec, V. DNA modifications by antitumor platinum and ruthenium compounds: their recognition and repair. Prog. Nucleic Acid Res. Mol. Biol. 2002, 71, 1-68
22. Leng M.; Locker D.; Giraud-Panis M. J.; Schwartz A.; Intini F. P.; Natile, G.; Pisano, C.; Boccarelli A.; Giordano, D.; Coluccia, M. Replacement of an NH(3) by an iminoether in transplatin makes an antitumor drug from an inactive compound. Mol. Pharmacol. 2000, 58, 1525-35.
23. Bierbach, U.; Sabat, M.; Farrell, N. Synthesis, crystal structure, and cytotoxicity of trans-[Pt(PyAc-N,O)Cl (NH3)]: Unprecedented inversion of the cis-geometry requirement for platinum-based antitumor complexes. Inorg. Chem. 2000, 39, 1882-1890.
24. Quintal, S. M. O.; Qu, Y.; Gomez-Quiroga, A.; Moniodis, J.; Nogueira, H. I. S.; Farrell, N. Pyridine-carboxylate complexes of platinum. Effect of N,O-chelate formation on model bifunctional DNA-DNA and DNA-protein interactions. Inorg. Chem. 2005, 44, 5247-5253.
25. Bierbach, U.; Farrell, N. Structural and reactivity studies on the ternary system guanine/methionine/trans-[PtCl2 (NH3)L] (L=NH3, quinoline): implications for the mechanism of action of nonclassical trans-platinum antitumor complexes. J. Biol. Inorg. Chem. 1998, 3, 570-580.
26. Souchard, J. P.; Wimmer, F. L.; Ha, T. T. B.; Johnson, N. P. A rapid method for the synthesis of water-soluble platinum(II) amine and pyridine complexes. J. Chem. Soc., Dalton Trans. 1990, 307-310.
27. trans-[Pt(OAc)2(NH3)(quin)] 1H NMR in D2O: 9.71 (d, 1 H), 9.24 (d, 1 H), 8.48 (d, 1 H), 8.10 (m, 1 H), 7.75 (m, 1 H), 7.57 (m, 1 H), 1.80 (s, 6 H). Anal. Calcd. (Found) for C13H16N2O4Pt: % C, 33.99 (33.97); % H, 3.51 (3.12); % N, 6.10 (6.02); % Cl, 0.00 (0.21).
Purity by HPLC: >99.9% pure (H2O, MeOH mobile phase).

Trans-[Pt(OAc)2(NH3)(iquin)] 1H NMR in CD3OD: d 9.20 to 7.63, iquin region; 4.38 (br), NH3; 1.85 (s), 2(O2CCH3). 1H NMR in D2O: d 9.12 to 7.76 iquin region; 2.00 (s), 2(O2CCH3). Anal. Calcd. (Found) for C13H16N2O4Pt. (H2O): % C, 32.71 (32.44); % H, 3.80 (3.41); % N, 5.87 (5.75); % Cl, 0.00 (0.12). Purity by HPLC: 100% pure (H2O, MeOH mobile phase).

trans-[Pt(OAc)2(NH3)2] Anal. Calcd. (Found) for C4H12N2O4Pt: % C, 13.84 (13.93); % H, 3.48 (2.94); % N, 8.07 (8.18); Cl, 0.00 (<0.10).

trans-[Pt(OAc)2(py)2] Anal. Calcd. for C14H16N2O4Pt: % C, 35.67; % H, 3.42; % N, 5.94.

Found: % C, 35.67; % H, 3.18; % N, 5.78. 1H NMR: d.1H NMR in CD3OD: (CD3OD): d 8.67 (d, 2 H, 2 H2,6), 7.98 (t, 1 H, H4), 7.51 (t, 2 H, 2 H3,5), 1.88 (s, 6 H, O2CCH3). Purity by HPLC: 99.4% (gradient elution profile H2O/CH3CN 15:85).

28. Bemers-Price, S. J.; Frenkiel, T. A.; Frey, U.; Ranford, J. D.; Sadler, P. J. J. Chem. Soc., Chem. Comm. 1992, 789-791.
29. Appleton, T. G.; Bailey, A. J.; Bamlham, K. J.; Hall, J. R. Aspects of the Solution Chemistry of trans-Diammineplatinum(II) Complexes. Inorg. Chem. 1992, 31, 3077-3082.
30. McGowan, G., Parsons, S.; Sadler, P. J. The contrasting chemistry of cis and trans PtII diamine anticancer compounds: hydrolysis studies of picoline complexes.
31. Canovese, L.; Cattalini, L.; Chessa, G.; Tobe, M. L., Kinetics of the displacement of cyclobutane-1,1-dicarboxylate from diammine(cyclobutane-1,1-dicarboxylato)platinum(II) in aqueous solution. J. Chem Soc., Dalton Trans. 1988, 2135-2140.
32. Frey, U.; Ranford, J. D.; Sadler, P. J. Ring-opening reactions of the anticancer drug carboplatin: NMR characterization of cis-[Pt(NH3)2(CBDCA-O)(5'-GMP-N7)] in solution. Inorg. Chem. 1993, 32, 1333-1340.
33. Pizarro, A. M.; Munk, V. P.; Navarro-Ranninger, C.; Sadler, P. J., Hydrolysis triggers oxidation of a trans Diamine Platinum(II) Anticancer Complex. Angew. Chem. Int. Ed., 2003, 42, 5339-5342.
34. Miller, S. E.; House, D. A. The hydrolysis products of cis-diammine-dichloroplatinum(II). 2. The kinetics and formation and anation of the cis-diamminedi(aqua)platinum(II) cation. Inorg. Chim. Acta 1989, 166, 189-197.
35. Segal, E.; Le Pecq, J. B. Role of ligand exchange processes in the reaction kinetics of the antitumor drug cis-diaminedichloroplatinum(II) with its targets. Cancer Res. 1985, 45, 492-497.
36. Marti, N.; Hoa, G. H.; Kozelka, J. Reversible hydrolysis of [PtCl(dien)]+ and [PtCl(NH3)3]+. Determination of the rate constants using UV spectrophotometry. Inorg. Chem. Commun. 1988, 1, 439-.445
37. Canovese, L.; Cattalini, L.; Chessa, G.; Tobe, M. L.; Kinetics of the displacement of cyclobutane-1,1-dicarboxylate from diammine(cyclobutane-1,1-dicarboxylato)platinum(II) in aqueous solution. J. Chem. Soc., Dalton Trans. 1988, 2135-2140.
38. Canovese, L.; Cattalani, L.; Gemelli, L.; Tobe, M. L. Acid- and base-catalyzed displacement of the carboxylate ligand from [Pt(dien)(RCO2)]+(dien=1,5-diamino-3-azapentane; R=CH2Cl, CHCl2, or CCl3) in aqueous solution. J. Chem. Soc., Dalton Trans. 1988, 1049-1052.
39. Murphy, R. F.; Farrell, N.; Aguila, A.; Okada, M.; Balis, F. M.; Fojo, T. Accumulation of novel transplatinum complexes in cisplatin and oxaliplatin resistant cell lines overcomes resistance. Proc. AACR, 2005, 4109.
40. Fojo, T.; Farrell, N.; Orthuzar, W.; Tanimura, H.; Stein, J.; Myers, T. G. Identification of non-cross-resistant platinum compounds with novel cytotoxicity profiles using the NCI anticancer drug screen and clustered image map visualizations. Crit. Rev. Hematol. Oncol. 2005, 53, 25-34.

Example 6

Effect of Carboxylate Leaving Groups and Steric Hindrance on Chemical and Biological Properties of Trans-Platinum Planar Amine Compounds Replacement of $NH_3$ by a planar amine L to give trans-[$PtCl_2$(L)(L')] (L=$NH_3$, L'=pyridine or substituted pyridine, quinoline, isoquinoline, thiazole; L=L'=pyridine, thiazole), greatly enhances the cytotoxicity of the transplatinum geometry. The "parent" compound trans-[$PtCl_2(NH_3)_2$] is therapeutically inactive. Modification of the ligands to an [$N_2O_2$] donor set, where O represents an acetate leaving group, enhances aqueous solubility whilst retaining the cytotoxicity of the parent chloride compounds. The effect of two mutual trans leaving groups but with weak trans influence is to impart remarkable chemical stability on the structure. This strategy is analogous to the use of the inert dicarboxylate leaving groups in the clinical compounds carboplatin and oxaliplatin. In this paper, systematic modification of the steric effects of carrier pyridine groups and, especially, carboxylate leaving groups in trans-[$Pt(O_2CR)_2(NH_3)(pyr)$] is shown to modulate aqueous solubility and hydrolysis to the activated aqua species. The results presented here demonstrate the utility of the "carboxylate strategy" in "fine-tuning" the chemical and pharmacokinetic properties in the design of clinically relevant transplatinum complexes.

Platinum complexes in the trans geometry are of interest for their biological properties. Substitution of $NH_3$ in trans-[$PtCl_2$(L)(L')] gives complexes with cytotoxicity in the micromolar range. Since the first publication of this phenomenon using planar amines 1-3 (pyridine, thiazole, quinoline, isoquinoline etc.) a range of amine ligands have been employed, including iminoethers, alicyclic amines and heterocyclic aliphatic amines.[4-8] In general, these complexes exhibit enhanced cytotoxicity with respect to the parent transplatin and are usually non-cross-resistant with cisplatin. Complexes containing Trans-Planar Amines (TPA compounds) exhibit a unique cytotoxicity profile in the National Cancer Institute (NCI) tumor panel and induce topoisomerase I-DNA complexes in human tumor cells.[9-10] To address the poor aqueous solubility and relatively high chemical reactivity of the trans-[$PtCl_2$(L)(L')] structure we have introduced the use of carboxylates as leaving groups in the first examples of cytotoxic transplatinum complexes containing [$N_2O_2$] ligand donor sets.[11] Complexes such as. trans-[$PtOAc)^2(pyr)^2$] are very water-soluble and surprisingly stable toward hydrolysis—resembling carboplatin in their reactivity. As a series, the complexes are cytotoxic in both cisplatin and oxaliplatin-resistant cells and show remarkably high cellular uptake.[11,12]

In Example 5 we suggested that the "carboxylate strategy" could be extended to all classes of transplatinum complexes. A report on some simple examples, using compounds containing the alicyclic amine motif,[13] analogs of compounds first developed by Navarro-Raninger et al.,[7] has since confirmed this suggestion.

The pharmacological properties of trans-[$Pt(O_2CR)_2$(L)(L')] can in principle be modified by steric and electronic effects of the donor groups as well as in the leaving carboxylate ligands. In this example, we report on the synthesis and characterization of a structurally similar set, trans-[Pt(O$_2$CR)$_2$(NH$_3$)(L)], and show that systematic variation of donor ligand (L=pyridine or substituted pyridine, 2-pic, 3-pic, or 4-pic) and R allows for a range of aquation rates and also cytotoxicity. Thus the general [PtN$_2$O$_2$] structure is capable of "fine-tuning" to enhance biological activity.

Figure 2:
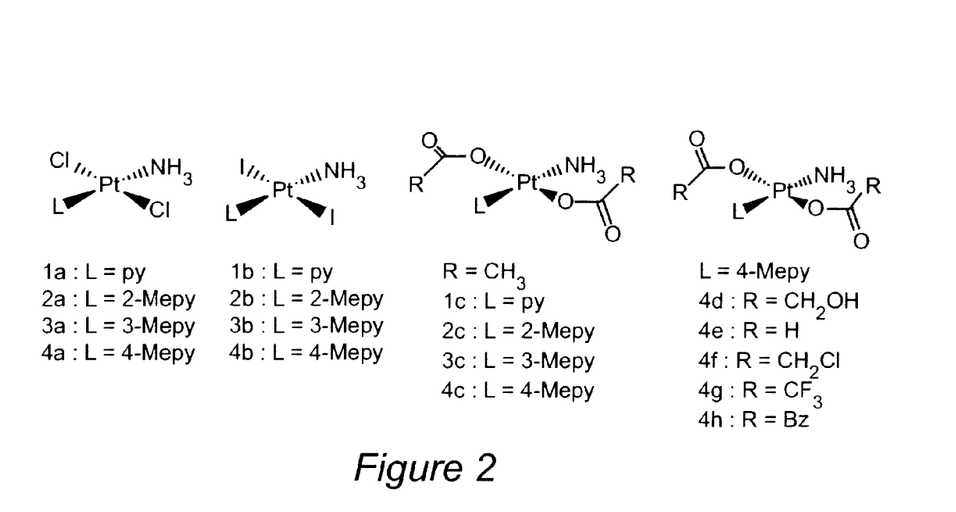
FIG. 2. TPA carboxylate compounds studied for Example 6.

The platinum complexes from this study are presented in FIG. 2. The synthesis and characterization of the intermediates and complexes 1a-c,[11] 2a, 3a & 4a,[14] 3b-c & 4b-c[12] have been previously reported. The syntheses of complexes 2b, 2c,[16] 4d,[17] 4e,[18] 4f,[19] 4g[20] and 4h were adapted from literature procedures,[11] and purity was confirmed by HPLC.[22] The $^1$H NMR chemical shifts and elemental analysis of these compounds is reported in the supplementary information. The silver salts of the carboxylates were prepared as described below.[15] The pathway to the final carboxylate complex takes advantage of the increased trans influence of the halides over the N-donor ligands. In all examples, synthesis from the chloride complex to the iodide intermediate was quantitative in yield, and yields of the final carboxylate complexes were much higher (50-70%) compared to recently published methods.[13]

TABLE 1

Solubility of TPA Carboxylates and pKa of the Corresponding TPA Diaqua Complexes at Ambient Temperature.

| | TPA Acetates | | | TPA Substituted Carboxylates | |
|---|---|---|---|---|---|
| | p$K_{a1}$ | p$K_{a2}$ | Solubility (mg/mL) | | Solubility (mg/mL) |
| 1c[11] | 3.73 | 6.8 | 11.6 | 4d | 22 |
| 2c | 4.03 | 7.1 | 10 | 4 | 35 |
| 3c[11,14] | 3.97 | 6.78 | 11.4 | 4f | 0.29 |
| 4c[11,14] | 3.94 | 6.88 | 13.2 | 4g | Insoluble |
| | | | | 4h | Insoluble |

The solubility of the complex series was measured at 37° C. and is presented in Table 1. Replacement of the halogens with acetate ligands significantly enhanced the aqueous solubility of TPAs as previously reported.[11] Aqueous solubility of the acetate series is influenced by the steric hindrance of the heterocycle (pyridine, quinoline etc.) [11] but there is little difference seen for the various substitution patterns around the pyridine ring. In contrast, significant differences are noted upon changing the carboxylate group. For the series of 4-pic complexes, increase in hydrogen bonding capability leads to enhanced solubility as seen for the formate 4e and hydroxyacetate 4d derivatives, while the chloroacetate 4f, trifluoroacetate 4g and benzoate 4h derivatives show reduced solubility.

The pKa of 1c was determined from the potentiometric titration of solutions of trans-[Pt(H$_2$O)$_2$(L)(L')]$^{2+}$ as per Ma.[11] This is presented Table 1 in comparison to the pKa values of the other compounds of the series 2-4c. The result is consistent with previous data[11,14] and confirms the effect on pKa1 of substitution of an ammine NH$_3$ or diamine (ethylenediamine, 1,2-diaminocyclohexane) by a π-acceptor ligand.[14,24]

Figure 3:
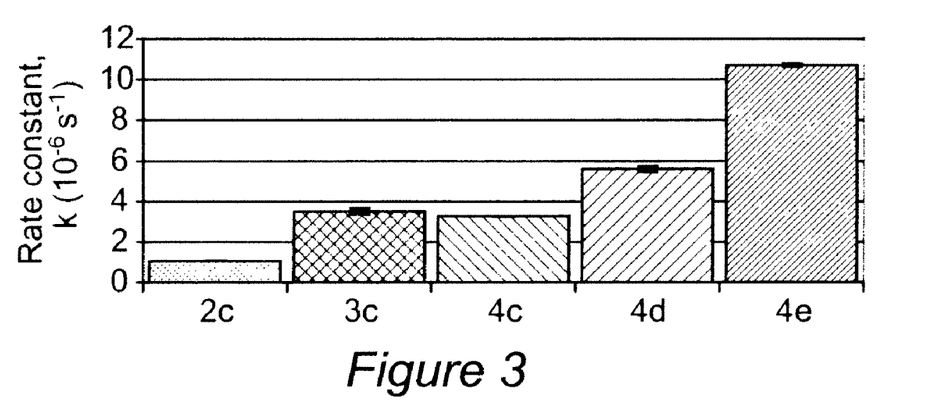
FIG. 3. Initial hydrolysis rate constants determined from HPLC experiments in $H_2O$ at 37° C.

The initial hydrolysis of selected TPA carboxylates (2-4c, 4d, 4e) was monitored by HPLC over a period of 12 h at 37° C., and initial hydrolysis rate constants were calculated using the program SCIENTIST (Version 2.0, MicroMath, Inc.) and are presented in FIG. 3. The slowest initial hydrolysis rate was found for complex 2c t-[Pt(OAc)$_2$(NH$_3$)(2-pic)], with just 4% hydrolysis occurring after 9 h. The hydrolysis of the formate complex 4f was the fastest, with 24% hydrolysis occurring after 9 h. The hydrolysis rates of the acetate complexes followed the pattern 2c<4c<3c. These results may be contrasted with those for the analogous dichloride complexes where the first hydrolysis step for formation of the monoaqua complex is relatively fast with k$_1$=2.6, 12.7 and 5.2×10$^{-5}$ s$^{-1}$ (I=0.1 M) for 2-pic, 3-pic and 4-pic respectively.[14] In contrast, the rates observed for the analogous acetate derivatives were k$_1$=1.07, 3.52 and 3.26×10$^{-6}$ s$^{-1}$ (I=0.02 M) for 2c, 3c and 4c respectively. Thus, hydrolysis of the acetate complexes is slowed by an approximate order of magnitude compared to their direct chloro analogs but there is little difference in the present case between 3- and 4-picoline. Steric hindrance therefore predominates over the electronic effects of the methyl group. In the case of the chloride complexes, the 3-pic directs less electron density to the platinum rendering it less nucleophilic relative to the 2-pic and 4-pic. 14 We observe the same trend in the acetate complexes, but the effect is lessened due to the carboxylate group being a weak ligand, with a low trans influence and trans effect.[11]

The hydrolysis rates of the carboxylate complexes followed the same pattern as the solubility, with 4c<4d<4e and values of k$_1$=3.26, 5.61 and 10.7×10$^{-6}$ s$^{-1}$ (I=0.02 M) respectively. The measured rate of 10.7×10$^{-6}$ s$^{-1}$ for the formate complex 4e is still slower than that of the chloro-analog and even that of cisplatin (51.8×10$^{-6}$ s$^{-1}$ at 20° C.).[25]

The slow hydrolysis is a unique feature of two carboxylate ligands in a trans-axial position and can be modulated by choice of carboxylate. To examine how this might affect possible reactions with biomolecules, a preliminary study of the reactions of 4e with guanosine-5'-monophosphate (5'-GMP, model for DNA) and N-acetyl-L-methionine (N-Ac-Met, model for sulfur ligand metabolism) was made by $^{195}$Pt NMR Spectroscopy. In the case of 5'-GMP the peak of the starting material at −1450 ppm is only gradually replaced by a new peak at −2365 ppm. This shift is consistent with the formation of a species that has a PtN$_4$ coordination sphere,[26] due to replacement of both formate groups. Approximately 50% reaction (as judged by the intensity of the $^1$H H8 signal and $^{195}$Pt NMR signals), occurred within 24h. For N-AcMet the starting material was approximately 50% of total intensity even after 8 h. A new species was observed with δ($^{195}$Pt) at −1775 ppm, which formed after one hour, and did not exceed 15% of the total reaction product over 10 h. The chemical shift is consistent with a PtN$_2$O$_2$ coordination sphere—this could arise from displacement of formate by H$_2$O/OH or an O-bound methionine.[27] This species preceded the formation of the N-AcMet product at −3320 ppm consistent with a PtN$_2$S$_2$ coordination sphere, trans-[Pt(NH$_3$)(4-pic)(NAc-Met)$_2$],[23,28] which was 40% of the total platinum species after 10 h. This reaction can be contrasted to that of trans-[PtCl$_2$(NH$_3$)$_2$], whose reaction with N-AcMet is complete within 5 h.[28] These results emphasize the previously-made analogy between the transplatinum [N$_2$O$_2$] ligand donor set and carboplatin, and show that substitution reactions with potentially deactivating biomolecules may be significantly retarded in comparison with chloro analogs. Whether the possible formation of an O-bound methionine species is a reflection of the low pKa1 and the electronic effects of a π-acceptor ligand is worthy of further investigation.

Figure 4:
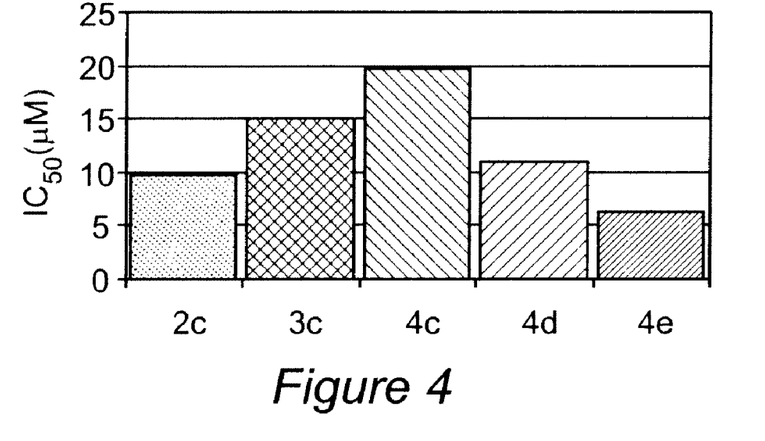
FIG. 4. Cytotoxicity in A2780 Human Ovarian Cells of the TPA carboxylate compounds.

The MTT assay was used to determine growth inhibition of the platinum drugs in the human ovarian cancer cell line A2780.[29] All TPA carboxylates tested exhibit cytotoxic behavior in the micromolar range. The most cytotoxic compound, 4e, trans-[Pt(OFm)$_2$(NH$_3$)(4-pic)], was also that which displayed the fastest hydrolysis, as well as being most soluble, FIG. 4. The cytotoxicity of the carboxylate compounds increases in the order 4c<4d<4e (OAc<OAcOH<OFm), suggesting that the nature of the carboxylate leaving group is related to cytotoxicity. The cytotoxicity of the acetate compounds increases in the order 2c<3c<4c (2-pic<3-pic<4-pic), suggesting that the steric hindrance of the methyl group can influence cytotoxicity, with the more sterically-hindered 2-pic complex being the most cytotoxic of the acetate compounds.

It is remarkable that the complexes with carboxylate leaving groups display, in general, cytotoxicity equivalent to the parent chlorides, despite their differences in reactivity.[1,2,12,14] In contrast, carboplatin is significantly less cytotoxic than cisplatin on a molar basis. Previous studies have shown significantly enhanced cellular uptake of the acetate derivatives[11,12] and it is reasonable to suggest that these results may reflect the overall modulation of the pharmacological properties responsible for cellular toxicity—uptake, nature and frequency of DNA adducts and the extent of metabolizing "deactivating" reactions. Thus, the results presented here demonstrate again the utility of the "carboxylate strategy" in the design of clinically relevant transplatinum complexes.

In summary, replacing an ammine in inactive trans-platin complexes with a planar amine greatly enhances the cytotoxicity, such as in trans-[$PtCl_2(NH_3)(L')$] (where L'=py, pic, iquin). Systematic modification of the steric effects of carrier pyridine groups and carboxylate leaving groups in trans-[$Pt(O_2CR)_2(NH_3)(pyr)$] is shown to modulate aqueous solubility and hydrolysis to the activated aqua species, while retaining cytotoxicity. Especially, the nature of the carboxylate ligand affects both hydrolysis (production of the pharmaceutically active aquated species) and cytotoxicity. Thus the "carboxylate strategy" is especially useful in "fine-tuning" the chemical and pharmacokinetic properties in the design of clinically relevant transplatinum complexes.

References for Example 7

(1) Van Beusichem, M.; Farrell, N. Inorg. Chem. 1992, 31, 634-639.
(2) Farrell, N.; Kelland, L. R.; Roberts, J. D.; Van Beusichem, M. Cancer Res. 1992, 52, 5065-5072.
(3) Farrell, N. Cancer Invest. 1993, 11, 578-589.
(4) Coluccia, M.; Nassi, A.; Loseto, F.; Boccarelli, A.; Mariggio, M. A.; Giordano, D.; Intini, F. P.; Caputo, P.; Natile, G. J. Med. Chem. 1993, 36, 510-512.
(5) Khazanov, E.; Barenholz, Y.; Gibson, D.; Najajreh, Y. J. Med. Chem. 2002, 45, 5196-5204.
(6) Najajreh, Y.; Perez, J. M.; Navarro-Ranninger, C.; Gibson, D. J. Med. Chem. 2002, 45, 5189-5195.
(7) Montero, E. I.; Diaz, S.; Gonzalez-Vadillo, A. M.; Perez, J. M.; Alonso, C.; Navarro-Ranninger, C. J. Med. Chem. 1999, 42, 4264-4268.
(8) Natile, G.; Coluccia, M. Coord. Chem. Rev. 2001, 216-217, 383-410.
(9) Fojo, T.; Farrell, N.; Ortuzar, W.; Tanimura, H.; Weinstein, J.; Myers Timothy, G. I Crit. Rev. Oncol./ Hematol. 2005, 53, 25-34.
(10) Murphy, R. F.; Farrell, N.; Aguila, A.; Okada, M.; Balis, F. M.; Fojo, T. Proc. Am. Assoc. Cancer Res. 2005, 46, [Abstract #4109].
(11) Ma, E. S. F.; Bates, W. D.; Edmunds, A.; Kelland, L. R.; Fojo, T.; Farrell, N. J. Med. Chem. 2005, 48, 5651-5654.
(12) Quiroga, A. G.; Perez, J. M.; Alonso, C.; Navarro-Ranninger, C.; Farrell, N. J. Med. Chem. 2006, 49, 224-231.
(13) van Zutphen, S.; Pantoja, E.; Soriano, R.; Soro, C.; Tooke, D. M.; Spek, A. L.; den Dulk, H.; Brouwer, J.; Reedijk, J. Dalton Trans. 2006, 1020-1023.
(14) McGowan, G.; Parsons, S.; Sadler, P. J. Inorg. Chem. 2005, 44, 7459-7467.
(15) AgOAcOH ($AgO_2CCH_2OH$, OAcOH=hydroxyacetate) was prepared by adding hydroxyacetic acid (0.0526 mol) to a suspension of $Ag_2O$ (4.32 mmol) in 150 ml $H_2O$. The mixture was stirred for 2 h in the dark, filtered through Celite and reduced until a white crystalline solid formed. Yield: 1.40 g (89%). AgOAcCl ($AgO_2CCH_2Cl$, OAcCl=chloroacetate), AgOFm ($AgO_2CH$, OFm=formate), AgTfa ($AgO_2CCF_3$, Tfa=trifluoroacetate) and AgOBz ($AgO_2CC_6H_5$, OBz=benzoate) were prepared similarly.
(16) trans-[$Pt(OAc)_2(NH_3)(2\text{-pic})$] 2c. $^{195}$Pt NMR ($d_6$-acetone) δ (ppm): −1420. IR (cm-1) 1633 m (C=O).
(17) trans-[$Pt(OAcOH)_2(NH_3)(4\text{-pic})$] 4d, $^{195}$Pt NMR ($D_2O$) δ (ppm): −1454. IR (cm-1) 1645 s (C=O).
(18) trans-[$Pt(OFm)_2(NH_3)(4\text{-pic})$] 4e, $^{195}$Pt NMR ($D_2O$) δ (ppm): −1450. IR (cm-1) 1614 s (C=O).
(19) trans-[$Pt(OAcCl)_2(NH_3)(4\text{-pic})$] 4f, $^{195}$Pt NMR ($CD_3OD$) δ (ppm): −1403. IR (cm-1) 1619 s, 1645 m, 1668 m (C=O).
(20) trans-[$Pt(Tfa)_2(NH_3)(4\text{-pic})$] 4g, $^{195}$Pt NMR ($CD_3OD$) δ (ppm): −1402. IR (cm-1) 1680, 1705 d, s(C=O).
(21) trans-[$Pt(OBz)_2(NH_3)(4\text{-pic})$] 4h, $^{195}$Pt NMR ($CD_3OD$) δ (ppm): −1420, IR (cm-1) 1633 m, 1620 m (C=O).
(22) RP HPLC, C18 Hydrosphere column (Phenomenex), Water/Acetonitrile gradient
(23) Norman, R. E.; Ranford, J. D.; Sadler, P. J. Inorg. Chem. 1992, 31, 877-888.
(24) Summa, N.; Schiessl, W.; Puchta, R.; van Eikema Hommes, N.; van Eldik, R. Inorg. Chem. 2006, 45, 2948-2959.
(25) Miller, S. E.; House, D. A. Inorg. Chim. Acta. 1989, 166, 189-197.
(26) Fontes, A. P. S.; Oskarsson, A.; Loevqvist, K.; Farrell, N. Inorg. Chem. 2001, 40, 1745-1750.
(27) Barnham, K. J.; Frey, U.; Murdoch, P. d. S.; Ranford, J. D.; Sadler, P. J.; Newell, D. R. J. Am. Chem. Soc. 1994, 116, 11175-11176.
(28) Oehlsen, M. E.; Hegmans, A.; Qu, Y.; Farrell, N. J. Biol. Inorg. Chem. 2005, 10, 433-442.
(29) 6500 cells per well, 37° C./5% $CO_2$, 72 h. $IC_{50}$ values were determined graphically While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:

1. A trans-platinum (II) complex of formula trans-[Pt(carboxylato)$_2$(L)(L')] where carboxylato =a ligand derived from an anion of a carboxylic acid, and wherein said trans-platinum (II) complex is represented by formula (I) as follows:

wherein
i) RCOO— is a carboxylate anion of a carboxylic acid and R is H or an alkyl group which may be substituted or unsubstituted; and
ii) L and L' are both planar heterocyclic amines, or one of L or L' is a planar heterocyclic amine and the other is selected from the group consisting of $NH_3$ a branched aliphatic amine, an iminoether, a primary amine, a secondary amine and an aliphatic nitrogen-containing heterocycle.

2. The trans-platinum (II) complex of claim 1, wherein L is a planar amine and L' is $NH_3$.

3. The trans-platinum (II) complex of claim 1, wherein the aliphatic nitrogen-containing heterocycle is selected from the group consisting of piperazine, piperidine and pyrazole.

4. The trans-platinum(II) complex of claim 1, wherein said carboxylato ligand is selected from the group consisting of formate, acetate, hydroxyacetate, chloroacetate, trifluoroacetate and lactate including optical isomers thereof.

5. The trans-platinum (II) complex of claim 1, wherein said planar heterocyclic amine is selected from the group consisting of pyridine, substituted pyridines, quinoline, subsituted quinolines, isoquinoline, substituted isoquinolines, thiazole, and substituted thiazoles.

6. The trans-platinum (U) complex of claim 1, wherein R is H or an alkyl group which may be substituted or unsubstituted.

7. The trans-platinum (II) complex of claim 1, wherein L or L' is substituted with a substituent selected from the group consisting of Me, Br, Cl and F.

8. The trans-platinum (II) complex of claim 1, wherein said trans-platinum (II) complex is selected from the group consisting of:
trans-[Pt(OAc)$_2$(NH$_3$)(py)]
trans-[Pt(OAc)$_2$(NH$_3$)(2Me-py)]
trans-[Pt(OAc)$_2$(NH$_3$)(3Me-py)]
trans-[Pt(OAc)$_2$(NH$_3$)(4Me-py)]
trans-[Pt(OAc)$_2$(NH$_3$)(tz)]
trans-[Pt(OAc)$_2$(NH$_3$)(quin)]
trans-[Pt(OAc)$_2$(NH$_3$)(Iq)]
trans-[Pt(OFm)$_2$(NH$_3$)(py)]
trans-[Pt(OFm)$_2$(NH$_3$)(2Me-py)]
trans-[Pt(OFm)$_2$(NH$_3$)(3Me-py)]
trans-[Pt(OFm)$_2$(NH$_3$)(4Me-py)]
trans-[Pt(OFm)$_2$(NH$_3$)(tz)]
trans-[Pt(OFm)$_2$(NH$_3$)(quin)]
trans-[Pt(OFm)$_2$(NH$_3$)(Iq)]
trans-[Pt(lact)$_2$(NH$_3$)(py)]
trans-[Pt(lact)$_2$(NH$_3$)(2Me-py)]
trans-[Pt(lact)$_2$(NH$_3$)(3Me-py)]
trans-[Pt(lact)$_2$(NH$_3$)(4Me-py)]
trans-[Pt(lact)$_2$(NH$_3$)(tz)]
trans-[Pt(lact)$_2$(NH$_3$)(quin)]
trans-[Pt(lact)$_2$(NH$_3$)(Iq)]
trans-[Pt(OAcOH)$_2$(NH$_3$)(py)]
trans-[Pt(OAcOH)$_2$(NH$_3$)(2Me-py)]
trans-[Pt(OAcOH)$_2$(NH$_3$)(3Me-py)]
trans-[Pt(OAcOH)$_2$(NH$_3$)(4Me-py)]
trans-[Pt(OAcOH)$_2$(NH$_3$)(tz)]
trans-[Pt(OAcOH)$_2$(NH$_3$)(quin)]
trans-[Pt(OAcOH)$_2$(NH$_3$)(Iq)]
trans-[Pt(TFA)$_2$(NH$_3$)(py)]
trans-[Pt(TFA)$_2$(NH$_3$)(2Me-py)]
trans-[Pt(TFA)$_2$(NH$_3$)(3Me-py)]
trans-[Pt(TFA)$_2$(NH$_3$)(4Me-py)]
trans-[Pt(TFA)$_2$(NH$_3$)(py)]
trans-[Pt(TFA)$_2$(NH$_3$)(quin)]
trans-[Pt(TFA)$_2$(NH$_3$)(Iq)]
trans-[Pt(OAc)$_2$(py)$_2$]
trans-[Pt(OAc)$_2$(2Me-py)$_2$]
trans-[Pt(OAc)$_2$(3Me-py)$_2$]
trans-[Pt(OAc)$_2$(4Me-py)$_2$]
trans-[Pt(OAc)$_2$(tz)$_2$]
trans-[Pt(OFm)$_2$(py)$_2$]
trans-[Pt(OFm)$_2$(2Me-py)$_2$]
trans-[Pt(OFm)$_2$(3Me-py)$_2$]
trans-[Pt(OFm)$_2$(4Me-py)$_2$]
trans-[Pt(OFm)$_2$(tz)$_2$]
trans-[Pt(lact)$_2$(py)$_2$]
trans-[Pt(lact)$_2$(2Me-py)$_2$]
trans-[Pt(lact)$_2$(3Me-py)$_2$]
trans-[Pt(lact)$_2$(4Me-py)$_2$]
trans-[Pt(lact)$_2$(tz)$_2$]
trans-[Pt(OAcOH)$_2$(py)$_2$]
trans-[Pt(OAcOH)$_2$(2Me-py)$_2$]
trans-[Pt(OAcOH)$_2$(3Me-py)$_2$]
trans-[Pt(OAcOH)$_2$(4Me-py)$_2$]
trans-[Pt(OAcOH)$_2$(tz)$_2$]
trans-[Pt(TFA)$_2$(py)$_2$]
trans-[Pt(TFA)$_2$(2Me-py)$_2$]
trans-[Pt(TFA)$_2$(3Me-py)$_2$]
trans-[Pt(TFA)$_2$(4Me-py)$_2$] and
trans-[Pt(TFA)$_2$(tz)$_2$]
wherein
OAc=acetate $CH_3COO^-$; OFm=formate $HCOO^-$; Lact=lactate $CH_3C.H(OH)COO^-$(.=R or S chirality); OAcOH=hydroxyacetate $HOCH_2COO^-$; TFA=trifluoroacetate $CF_3COO^-$; py=pyridine; 2Me-py=2-methylpyridine; 3Me-py=3-methylpyridine; 4Me-py=4-methylpyridine; tz=thiazole; Iq=isoquinoline; and quin=quinoline.

* * * * *